(12) United States Patent
Johnson et al.

(10) Patent No.: US 10,037,821 B2
(45) Date of Patent: Jul. 31, 2018

(54) SYSTEM FOR INTEGRATED PROTOCOL AND DECISION SUPPORT

(71) Applicant: GENERAL ELECTRIC COMPANY, Schenectady, NY (US)

(72) Inventors: Christopher Donald Johnson, Niskayuna, NY (US); Kunter Seref Akbay, Niskayuna, NY (US); Brian McIlroy, Albany, NY (US); Roxana Malladi, Bangalore (IN); Paulo Gallotti Rodrigues, Rio de Janeiro (BR); Marcelo Blois Ribeiro, Rio de Janeiro (BR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 280 days.

(21) Appl. No.: 14/141,706

(22) Filed: Dec. 27, 2013

(65) Prior Publication Data
US 2015/0187038 A1    Jul. 2, 2015

(51) Int. Cl.
*G16H 50/20*   (2018.01)
*G06Q 50/24*   (2012.01)
*G06Q 30/02*   (2012.01)
*G06Q 10/06*   (2012.01)

(52) U.S. Cl.
CPC ....... *G16H 50/20* (2018.01); *G06Q 10/06316* (2013.01); *G06Q 10/06395* (2013.01); *G06Q 10/063118* (2013.01); *G06Q 30/0203* (2013.01); *G06Q 50/24* (2013.01)

(58) Field of Classification Search
None
See application file for complete search history.

(56) References Cited

U.S. PATENT DOCUMENTS

| 4,937,743 | A | * | 6/1990 | Rassman | G06F 19/327 345/441 |
| 5,319,363 | A |   | 6/1994 | Welch et al. | |
| 5,706,441 | A | * | 1/1998 | Lockwood | G06Q 30/02 705/2 |

(Continued)

OTHER PUBLICATIONS

Jh,"Building a Better Delivery System: A New Engineering/Health Care Partnership", National Academy of Engineering (US) and Institute of Medicine (US) Committee on Engineering and the Health Care System, 2005.

(Continued)

*Primary Examiner* — Jonathan Ng
*Assistant Examiner* — Rachelle L Reichert
(74) *Attorney, Agent, or Firm* — GE Global Patent Operation; Pabitra Chakrabarti

(57) ABSTRACT

Embodiments of the system support hospital operations, delivery of health care, and improve patient satisfaction. The interactive hospital information system utilizes inputs from a mobile device, eliminating the cost of fixed cameras and sensor systems in the hospital facility. Aspects of the invention facilitate real-time patient care and patient room updates by care providers, validating that prescribed devices, services, and setups are in place per protocol. The system communicates with rounding persons as to specific care management. Network devices, such as an iPad® or smartphone, are utilized to monitor and record ongoing activities in the healthcare setting.

35 Claims, 10 Drawing Sheets

(56) References Cited

U.S. PATENT DOCUMENTS

| | | |
|---|---|---|
| 7,234,081 B2 | 6/2007 | Nguyen et al. |
| 7,324,081 B2 | 1/2008 | Friedrich et al. |
| 7,725,339 B1* | 5/2010 | Aykin ............ G06Q 10/06311 705/7.14 |
| 8,275,414 B1 | 9/2012 | Athsani et al. |
| 8,344,860 B2 | 1/2013 | Collins, Jr. et al. |
| 8,407,234 B1* | 3/2013 | Buschbach ............ G06Q 10/04 707/752 |
| 8,416,084 B2 | 4/2013 | Beltmann et al. |
| 8,500,636 B2 | 8/2013 | Tran |
| 8,612,272 B1* | 12/2013 | Aykin ................ G06Q 10/063 705/7.11 |
| 9,041,707 B2* | 5/2015 | Ferrara ................ G06T 11/00 345/418 |
| 2002/0077849 A1* | 6/2002 | Baruch ................ G06F 19/325 705/2 |
| 2002/0087361 A1* | 7/2002 | Benigno ............ G06F 19/325 705/3 |
| 2003/0033184 A1* | 2/2003 | Benbassat ............ G06Q 10/06 705/7.14 |
| 2003/0153818 A1* | 8/2003 | Bocionek ............ A61B 5/411 600/300 |
| 2004/0122711 A1* | 6/2004 | Miller .................. G06F 19/327 705/2 |
| 2004/0153344 A1* | 8/2004 | Bui ...................... G06F 19/323 705/3 |
| 2004/0190794 A1* | 9/2004 | Belanger ............ G06F 17/3025 382/305 |
| 2004/0202349 A1* | 10/2004 | Erol .................. G06F 17/30256 382/100 |
| 2005/0246314 A1* | 11/2005 | Eder .................. G06F 19/3437 |
| 2006/0022834 A1* | 2/2006 | Rosenfeld ............ G06F 19/325 340/573.1 |
| 2006/0038833 A1 | 2/2006 | Mallinson et al. |
| 2006/0053034 A1* | 3/2006 | Hlathein ................ G06Q 50/22 705/2 |
| 2006/0074740 A1* | 4/2006 | Garcia .................. G06Q 10/06 705/7.14 |
| 2006/0143044 A1* | 6/2006 | Conry .................... G06Q 10/06 705/2 |
| 2006/0143060 A1* | 6/2006 | Conry .................... G06F 19/327 705/7.19 |
| 2006/0152358 A1 | 7/2006 | Osterweil |
| 2006/0210132 A1* | 9/2006 | Christiansen, II ... A61B 5/0059 382/128 |
| 2007/0038037 A1* | 2/2007 | Fors .............................. 382/128 |
| 2007/0162311 A1* | 7/2007 | Gentles .................. G06Q 10/00 706/19 |
| 2007/0168307 A1* | 7/2007 | Floudas ................ G06F 19/325 600/300 |
| 2008/0046292 A1* | 2/2008 | Myers ............... G06F 17/30557 705/3 |
| 2008/0140444 A1* | 6/2008 | Karkanias ............ G06Q 50/24 705/3 |
| 2008/0162182 A1* | 7/2008 | Cazares ................ G06Q 50/22 705/2 |
| 2008/0208015 A1* | 8/2008 | Morris ................ G06F 19/363 705/2 |
| 2008/0249376 A1* | 10/2008 | Zaleski ................ A61B 5/0006 600/301 |
| 2008/0300918 A1* | 12/2008 | Tenenbaum ......... A61B 5/0022 600/301 |
| 2009/0059270 A1* | 3/2009 | Opalach ............... G06Q 10/087 358/1.15 |
| 2009/0102859 A1* | 4/2009 | Athsani ................ G06Q 10/087 358/1.15 |
| 2009/0125337 A1* | 5/2009 | Abri ........................ G06F 3/011 345/619 |
| 2009/0177493 A1* | 7/2009 | Narayan ................ G06F 19/327 705/3 |
| 2009/0286570 A1 | 11/2009 | Pierce, Jr. |
| 2009/0313049 A1* | 12/2009 | Joao ...................... G06F 19/322 705/3 |
| 2010/0235228 A1* | 9/2010 | Torress ............ G06Q 10/06393 705/7.39 |
| 2010/0257252 A1 | 10/2010 | Dougherty et al. |
| 2010/0280839 A1* | 11/2010 | Katz ...................... G06Q 50/22 705/2 |
| 2011/0010087 A1* | 1/2011 | Wons ................... G06F 19/327 701/533 |
| 2011/0035253 A1* | 2/2011 | Mason .................. G06Q 10/06 705/7.13 |
| 2011/0119075 A1* | 5/2011 | Dhoble ................ G06F 19/322 705/2 |
| 2011/0125539 A1* | 5/2011 | Bollapragada ....... G06Q 10/043 705/7.12 |
| 2011/0133935 A1* | 6/2011 | Beltmann ............ A61B 5/1113 340/573.1 |
| 2011/0161113 A1* | 6/2011 | Rumak ............... G06F 19/3487 705/3 |
| 2011/0215933 A1* | 9/2011 | Darling, IV ......... G06Q 10/109 340/573.1 |
| 2011/0243459 A1* | 10/2011 | Deng ................... G06K 9/6203 382/218 |
| 2011/0306926 A1* | 12/2011 | Woo .................... G06F 3/0488 604/65 |
| 2011/0307266 A1* | 12/2011 | Henley ................ G06F 19/327 705/2 |
| 2012/0075464 A1* | 3/2012 | Derenne ............ A61B 5/0013 348/135 |
| 2012/0136671 A1* | 5/2012 | Alt ........................ G06F 19/327 705/2 |
| 2012/0154582 A1* | 6/2012 | Johnson ................ G06F 19/321 348/143 |
| 2012/0212582 A1* | 8/2012 | Deutsch ................ G08B 21/245 348/46 |
| 2012/0245948 A1* | 9/2012 | Nolte .................... G06Q 50/22 705/2 |
| 2012/0314901 A1* | 12/2012 | Hanson .............. A61B 5/1117 382/103 |
| 2013/0051611 A1* | 2/2013 | Hicks .................... G06T 11/60 382/103 |

OTHER PUBLICATIONS

"Quality of Care", WHO, 2006.

Rockville, "Patient Safety and Quality: An Evidence-Based Handbook for Nurses", Agency for Healthcare Research and Quality (US), pp. 1-18, 1146-1184, 1234-1396, 2008.

Vilamovska, "Improving the Quality and Cost of Healthcare Delivery", Pardee Rand Graduate School, pp. 1-279, May 2010.

"Intelligent Hospital Today", An on-line publication of the RFID in Healthcare Consortium, http://intelligenthospitaltoday.com/, Sep. 2013.

* cited by examiner

SYSTEM FOR INTEGRATED PROTOCOL AND DECISION SUPPORT

FIELD

The invention relates generally to hospital operations, patient satisfaction, and clinical care delivery workflow, more particularly to clinical care delivery using wireless and mobile platforms with augmented reality.

BACKGROUND

Hospitals deliver care to patients across the globe at a continuum of cost points. In developed countries, information acquisition to aid in the planning and delivery of care is generally possible with infrastructure investment having internal rates of return exceeding 25%. In developing locations, lack of capital reduces expenditure on infrastructure except for the actual facility or clinical treatment apparatus. Yet, labor is far less costly than in developed regions, thereby enabling manual information acquisition at cost points that are economically justified. A need exists in all markets to provide quality care at a cost point that is sustainable. Current systems provide methods for attaining patient status and delivering decision support as based on subjective input from hospital personnel and to a small extent, a patient's visitors when able to communicate effectively to the hospital staff. Where limited infrastructure is in place to collect patient information, information is lacking or not available to improve processes, facilitate care delivery and improve patient satisfaction. In addition, the use of subjective data input and any support systems typically fail to achieve a safe, high throughput capacity; and fail to have the objective data or infrastructure to minimize unavailable capital investment funds. Furthermore, in measures for clinical/patient protocols are inconsistent. The current systems acquire information through note-taking and deliver care based on individual hospital personnel notations in the medical record, and sometimes via subjective visitor feedback.

In developed regions, such as in the United States, health systems have financial reimbursement incentives to deliver a patient experience those patients deem as above average. Additionally, reimbursements are increasingly made in 'pay for performance' business models. As such, the clinical care quality must follow best practice protocols in order to avoid adverse hospital acquired conditions that will not be reimbursable. Further still, health institutions themselves increasingly serve as the insurer and therefore have strong financial incentives to enable better clinical outcomes, sooner. Therefore, capacity management, asset utilization, care delivery and patient experiences play a vital role in an environment where productivity proves paramount for financial vitality.

In developing regions, the most pressing need is to serve regional populations with capacity at very low cost points. Health systems do not have the capital to install clinical or operational infrastructure that would in turn improve the outcomes and productivity of their hospitals and clinics.

Hospital networks have various costs. A radiofrequency (RFID) system typically requires a plethora of stations for radio signal acquisition and/or triangulation. Other embodiments have infrared (IR) triggers, which then begin communication bursts for location establishment; such infrastructure, however, is more costly and involves possible interruption of clinical care during installation and maintenance. Tags, placed on care providers, patients and clinical assets are active or passive. The active tags are typically battery powered and can be re-used; thereafter, ongoing costs escalate as related to cleaning, workflow, shrinkage, and loss (as patients at discharge may not realize a personalized RFID unit is with them as they leave). Taken together, these systems can cost several hundred to several thousand dollars per room. The one time capital cost for base capability and the lifecycle costs of tag, battery and maintenance erodes the economic return related to the benefits of higher patient satisfaction, reduced adverse events, a reduction in missed consumables and improvements in protocol delivery.

Thus, a shared need exists across health systems globally to acquire location and state data of patients, physical assets, consumables, and staff while also providing interactive decision support to patients, staff, and various care stakeholders. The desirable system will increase productivity while also improving outcomes and a patient's experience.

A system is desired that would address the needs in monitoring overall patient care and patient satisfaction during a patient's hospitalization, from admittance through discharge. The system would be implemented with current systems including alerts and alarms as integrated in temporary, urgent and critical care, but also incorporate an ongoing real-time monitoring with a deliverable output report that objectively identifies provider-patient interaction, routine care, clinician-patient contact, ongoing contact with other individuals (in-hospital staff or family/friends), connectivity or disconnectivity with a network connection, and benefits or drawbacks as realized and associated with costs. The real-time monitoring system would be capable of storage, analysis, and reporting of select data as accessed and retrieved through a confidential network, using broadly commercially available assets.

The invention disclosed in the following addresses the issues as indicated above and further resolves the need for clinical systems that currently lack the monitoring and analytical capabilities that would prevent patient dissatisfaction and identify interactions that benefit a patient and his/her care plan.

SUMMARY

Embodiments of the invention encompass wireless and mobile platforms to effect hospital operations, patient satisfaction, and clinical care delivery workflow, more particularly clinical care delivery using augmented reality with real-time implementation. The system of the invention enables a broader participation of stakeholders in the delivery of optimized patient care.

The invention employs a system to address a patient's needs and desires during hospitalization, from admittance through discharge. In one embodiment, the system implements temporary, stepdown, home, urgent and critical care while incorporating low-cost fixed and variable real-time monitoring. A stepdown is a less acute care setting such as a recovery facility for physical therapy or assisted living, a bridge between a hospital and independent living (i.e. much more cost effective than in-patient care). A resulting output report objectively identifies provider-patient interaction, routine care patterns, clinician-patient contact, ongoing contact with other individuals (in-hospital staff or family/friends), connectivity or disconnectivity between people or clinical devices, and feedback with a Wi-Fi or cellular network connection. The report also enables the calculation of financials and patient outcomes (benefits or drawbacks) as realized and associated with the monitoring and care delivery system disclosed. The real-time monitoring system can store, analyze, and report select data as provided to, accessed and, retrieved through commercial devices and infrastructures such as smart phones and Wi-Fi networks in a confidential way via downloadable applications, permissions and encryption at the edge device and remote computing site.

The invention disclosed in the Detailed Description below addresses the issues as indicated above and further resolves the need for clinical systems that monitor and analyze patient data in real-time while taking the entire patient's decision making, interaction with others, treatment plan, medications, response times, movement and mobility, assist and non-assist events, and other patient events and activities that can be correlated with patient clinical outcomes, recovery rate, re-admissions, satisfaction, contentment, attitude, and feedback.

The present invention includes information acquisition, computer processing of complex process and protocol algorithms and stakeholder communication. Stakeholders include patients, staff, functional departments and visitors.

The disclosed invention uses commercially prevalent devices such as phones and tablets communicating via cell and Wi-Fi infrastructures to acquire location and state information of people, assets and consumables. Health system operations and patient care algorithms may be processed via off-premise computing assets. Feedback to patients, care providers, visitors, administrators, departmental stakeholders and assets is likewise delivered via commercial devices on low cost communications infrastructure. Specific superimposed instruction is provided such that more stakeholders in the care process, not necessarily highly skilled doctors and nurses, can participate in the processes of care, including a patient's visitors.

In one embodiment, a mobile device such as an iPad® connects to a hospital's Wi-Fi network, downloads a software application, continues through an authentication routine for the specifically identified user, and is then made acceptable for a specifically logged on individual to take a video or capture picture images and input. In one aspect, the disclosed system recognizes tags, patterns, or shapes and sends location, person ID, and objects identification back to the decision support system or works with the remote decision support system for image processing and augmented reality processing. The decision support system in one aspect manages beds, workflows, staffing, stakeholder schedule coverage, care, and protocol adherence. Using the same basic mobile device infrastructure to measure the distance between observed identification tags and/or objects, protocols are checked (e.g. bed rails up, bed lowered, tray nearby for water or other items to prevent the chances of a patient falling out of bed). Graphical or text notifications tell the person doing rounds what is wrong and what is okay with respect to the monitored protocols. Further, on same mobile device, basic data from the patient is recorded (i.e. by speaking with them or recording them speaking), as well as attaining information from family members or care providers via interactive user interfaces.

Embodiments of the system allow the patient and patient advocates to logon to the system with their personal device at admissions or a control desk, or self-directed instruction routine downloaded to the device. The mobile device is active for the duration of the patient's stay for continuously updating information, status, patient state or condition, and various input data. and the mobile device enables participation in specified directed aspects of care delivery (e.g. as related to patient satisfaction, patient comfort, placement information, asset location, consumables consumption, recording rounding, patient location, patient exercise, patient food consumption—what, how much and when, patient discharge instructions, among other factors as desired).

Using a mobile device with a camera and software to recognize tags based upon the tag's prescribed pattern, embodiments of the system measure the presence of items and geo-spatial positions in accordance with desired relationships as dictated by protocols and operational decision support. Protocol logic, workflow logic and operational decision support feeds into the system "as-is" identification and spatial information. The mobile device as an interface receives protocol, workflow, operational or other descriptive information back from the analytics which are computed locally, though remote access and analysis embodies one aspect as well. The mobile device is used to answer data input questions that are tailored based upon specific object or state interaction with respect to a care plan or protocol logic. Manual and automated data inputs such as patient satisfaction, family satisfaction, adequate medical supply, adequate state of machines or devices, clinical information, and operational information is reported. Dynamic input templates and question generation for the person handling the device elicits information as desired by hospital operations.

The interactive hospital information system utilizes inputs from a mobile device, eliminating the cost of fixed cameras and sensor systems in the hospital facility. Embodiments of the system eliminate information latency, except for times when hospital staff attain patient room updates or validate prescribed devices, provide services or setups per the protocols invoked as a part of the patient's care plan. The system enables lower skilled people and commercially available devices to also gather information. The system communicates with rounding persons employed by the hospital, clinical care providers, and other stakeholders (such as a patient's visitors) identifying missing information for care management and escalating workflows to attain missing information, if any. The lower cost of the disclosed physical monitoring enables the involvement of care stakeholders beyond paid hospital staff, effectively and efficiently. This offers several commercial advantages by lowering the cost of installed geo-spatial location infrastructure, enabling patient data acquisition by lower cost persons in the care process, and dynamically prompting care stakeholders with information required for workflows, patient state, and care set-up.

In an embodiment disclosed herein, network devices are utilized to monitor and record ongoing activities in the healthcare setting. Devices such as an iPad® or smartphone are integrated in one aspect and provide an easy, affordable, and objective measure of patient status. In one embodiment, multiple images are acquired and recorded for comparison with ongoing imaging, data records and patient interaction. Various configurations and modifications of the system can be made in accordance with mobile devices and personal computing with the integrated software and shared network structures.

As claimed, the invention disclosed is an integrated hospital information system for clinical decision support comprising: a plurality of data capture devices, each having manual data input and at least one of a visual sensor, audio sensor, or a light-based sensor to configure computer generated input of sound, video, graphics, global positioning (GPS), light-based detection laser-based detection, body scanning, or retinal scanning to provide a captured image of a patient's care and care setting; at least one storage unit in the form of a server or a cloud-based storage connected to a network; a processor comprising an analytics module that interacts with the at least one storage device and said plurality of data capture devices to compare the captured image with a protocol image to determine whether the captured image of the patient adheres to one or more of regulatory protocols, operating protocols, health provider orders, and a patient's treatment or care plan; and a user interface integrated with each of the plurality of data capture devices that refreshes the captured image in real-time; wherein each of the plurality of data capture devices comprises a network interface for internet access.

In one embodiment, the captured image is saved in the system as a prior image and overlaid by an updated captured image that provides overlaid action directives on the captured image and publishes on the network as a refreshed image that encompasses one or more action items or initiates real-time indicators to provide ongoing patient monitoring and reporting updates to stakeholders. The analytics module produces outputs that result in augmented or annotated information delivered to at least one of the data capture devices. In one aspect, the captured image is a real-world observation by a user of the data capture device and produces a real-time image that overlays a graphic of a hospital room environment with a defined protocol. In another aspect, the graphic of the hospital room environment identifies one or more deviations from the defined protocol, and the processor provides an alert at each of the user interfaces as integrated with each of the plurality of data capture devices including at least one of the site of the deviation, at a health care provider alert station, and on one or more mobile devices. The captured image is updated continuously as evidence as to whether a defined protocol has been followed or not.

In embodiments of the invention, the analytics module extracts a patient's identification and HIPAA information associated with a patient's identification tag or electronic medical record. The data capture device can be a mobile device of a clinician to provide protocol support, treatment plans, and feedback; or a mobile device of a patient to provide inputs into the system as to perceived well-being and status.

Various aspects of the system implement a mobile device that receives information from the network along with alerts, such that the information and resources are shared within a hospital unit or across multiple hospital units. Thus, a patient's electronic medical records as associated with a personalized treatment plan can be published within the network whenever inputs or modifications are made. In another aspect, a decision support system incorporated with the analytics module reports prior decisions made as to the personalized treatment plan, a prior patient's treatment or care plan, and further recommends options as to future treatment. Where a plurality of inputs and a plurality of outputs are analyzed and recorded in memory/storage for later recall and reporting, the patient feedback system can implement a survey as to patient satisfaction and overall hospital operations.

Embodiments of the invention utilize the integrated hospital information system for clinical decision support in a care setting comprising any one of: a hospital, a medical institute, a dental clinic, an outpatient clinic, a physician's office, a pharmaceutical setting, home environment, or other patient care setting. Therefore, the methods of using the system comprise a step of recording the captured image, and continually updating the captured image on the network such that the captured image is graphically overlaid by an updated captured image that is analyzed in relation to protocol. The updated captured image can then publish on the network to provide ongoing patient monitoring and reporting of updates. A method of utilizing the system further comprises a step of reporting updates that are further utilized as an ongoing score of processes being met satisfactorily or unsatisfactorily to provide a validation process during post-process analytics. Another method of using the system comprises scheduling coverage via mobile devices networked to the system to provide monitoring of directed care using one or more of a function of hospital staffing, type of services needed, and stakeholder availability. During the step of scheduling coverage, shift timing can be adjusted throughout a 24 hour timeframe to accommodate patient care and staffing objectives. Or in scheduling coverage, the staffing objectives can accommodate physician, nurse, and staff availability, including staff shortages, surpluses, overtime, and use of temporary or agency staff.

Overall, the system provides ongoing patient monitoring and reporting such that updates synchronize and publish to mobile devices, communication centers, and health care providers in the form of text, picture, video, call, or web-enabled interface on a continuous basis or as determined per protocol and communication support. A method of using the system utilizes a step of providing real-time patient care quality reports and a step of assessing a hospital's operational quality to produce patient satisfaction reports and hospital assessment, respectively. In one aspect, mixed integer linear programming provides optimization in the system as data and information is correlated while noise is reduced or eliminated. In another aspect, the mixed integer linear programming utilizes a task component such that staffing is monitored per patient caseload and a shift prescribed for a specified hour and within a particular hospital. The shift prescribed triggers an inquiry in the system for availability of staff, and creates new shifts or augments an existing shift by changing the duration, start time, end time, or allocation of staff within or across units. Staff are able to respond using the user interface to post and schedule real-time availability.

Further, the system utilizes a decision support framework in combination with protocols or patient care needs to make dynamic decisions concerning assignment of staff to patients. In one aspect, a target response is a control variable in a numerical simulation of a hospital care delivery process. A cost associated with meeting the target response time [target costs] can then be compared to a cost in relation to a variable response time [variable costs], such that the costs [target and variable] are correlated to a patient satisfaction score.

In addition, as described in various embodiments, the protocol image establishes a threshold protocol that is dynamically adjusted based on learned information about a patient such that a duration for a plurality of patients is a function of personality, descriptive attributes, staff, visitors, and attributes known or determined to affect patient feedback. The duration engages stakeholders including physicians, nurses, staff, skilled hospitality, administration and visitors.

Therefore in utilizing the system of the invention, the data capture device can be a fixed monitoring modality used to validate inputs from a plurality of mobile devices. One or more of regulatory protocols, operating protocols, health provider orders, and a patient's treatment or care plan, for exemplary purposes and not limitation, designate at least one visit, and thus the patient's care and care setting alerts the stakeholder as to a missed visit. The visit may be defined as any casual, medical, or prescribed treatment modality as described here.

While monitoring the patient's care and care setting in real-time, the integrated hospital information system stores, analyzes, and reports data with permissions and encryption with an edge device or by way of remote computing, and with the use of the plurality of data capture devices including mobile devices. As described herein, embodiments and aspects of the invention are modified and designed in accordance with provider needs, patient care plans, patient satisfaction and hospital quality assurance. The implementation of the system allows subjective information to be recorded and analyzed for objective evidence and analysis to create a real-time imaging awareness of care and treatment costs in healthcare.

BRIEF DESCRIPTION OF THE DRAWINGS

Features and aspects of embodiments are described below with reference to the accompanying drawings, in which elements are not necessarily depicted to scale.

DETAILED DESCRIPTION

Figure 1:
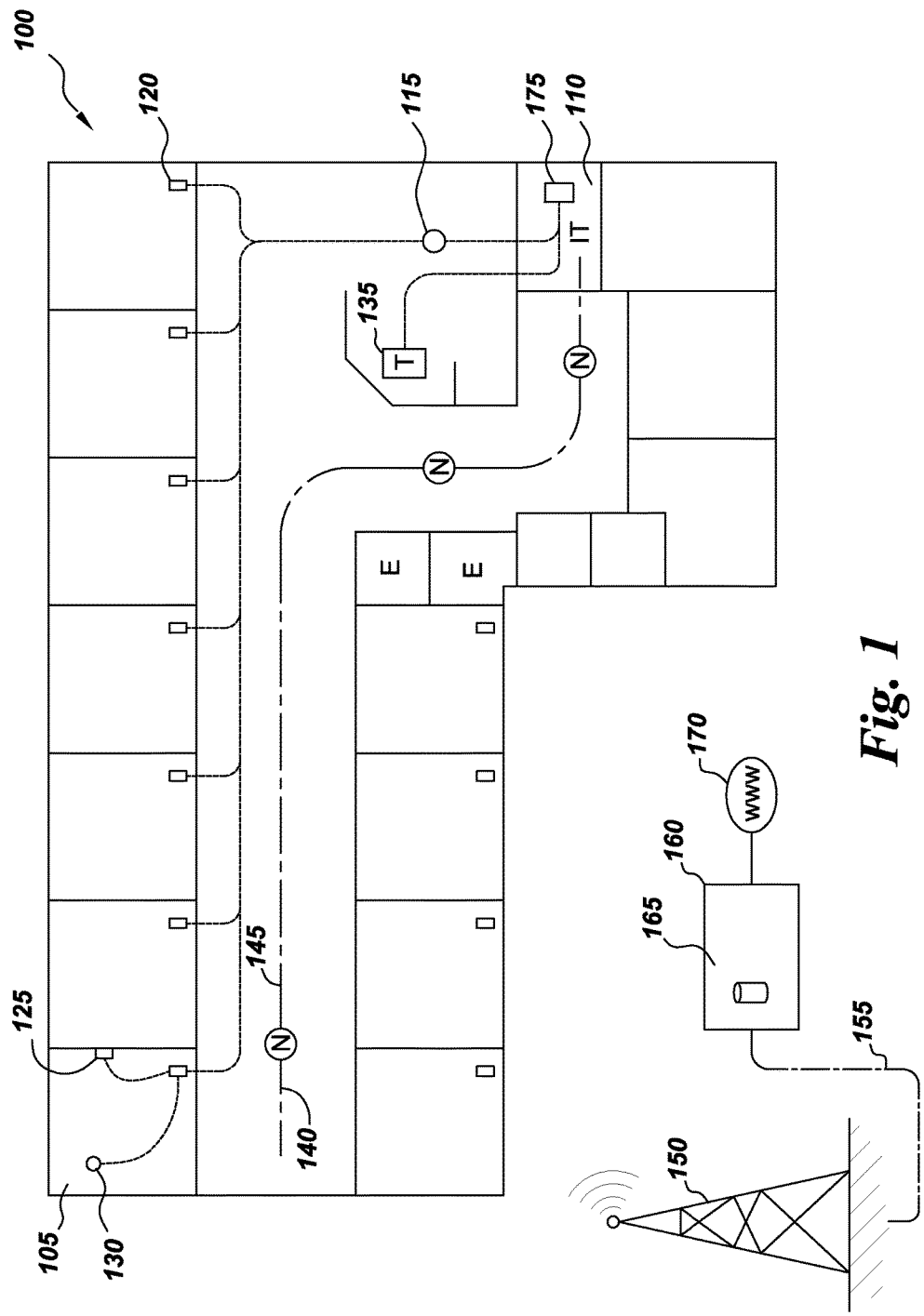
FIG. 1 illustrates one embodiment of an in-patient care system connected through various wireless network devices.

Embodiments are directed to systems and methods of improving a hospital's ability to direct clinical workflow and enhance capacity to improve management of patient care, safety, and patient satisfaction. The invention comprises an in-room data acquisition and computing system by way of in-room data capture devices and mobile devices coupled to a remote computing infrastructure with secure communication. Any number of images and recordings are integrated to monitor data of patient interaction with clinicians and providers of care, as well as with supporting assets and consumables, to deliver overall patient care and satisfaction. The mobile or fixed device systems include sensors such as in the use of camera(s), radio frequency (RF) readers, RF senders, infrared (IR) readers, IR senders, motion detectors, light level sensors and detectors, laser-based detectors, body or retinal scanners, microphones for sound sensing, speakers, variable light, color, or intensity in a voice. Further, the hospital information system and/or cellular network of a commercial provider supports clinical and hospital operations in connection with the sensor-based systems, mobile devices, and mobile device networks that use the disclosed system's software.

Terminology

Augmented Reality Systems

Augmented reality systems are live, direct or indirect views of a physical, real-world environment whose elements are augmented (or supplemented) by computer-generated sensory input such as sound, video, graphics or GPS data. Using image recognition, computer vision, and/or object recognition technology, the information about the surrounding real-world of the user becomes interactive and can be digitally manipulated. Virtual information about the environment and its objects can be overlaid on the real world view that the user sees as a composite image.

With advances in augmented reality technology, it has become possible for mobile devices such as smartphones and tablets equipped with cameras to capture the real world environment of a user. The mobile devices communicate with servers at the hospital, dedicated data centers, or the cloud that each run software programs to analyze the information and return annotative and augmented information to the network device. In one aspect, the data is overlaid on the user's view of the real-world as shown on the mobile device.

Tags

For the purposes of describing essential aspects of the invention, tags may be described as matrix or 2D barcodes. They may be references or fiduciary markers. A number of tags, for exemplary purposes and not limitation, include quick response (QR) codes, and Microsoft® tags, and/or augmented reality tags (ARTags) to mark objects in a hospital room. The aforementioned examples do not comprise an exhaustive list. In addition to the objects in a hospital room, the actual physical patient identification (ID) tags have matrix tags or 2D barcodes, fiducial or fiduciary markers marked on them. These barcodes are encoded with HIPAA (Health Insurance Portability and Accountability Act) compliant authorization and access information. Information about surveys, patient satisfaction, scheduling, and administrative use may also be integrated with the tag.

System

The invention uses a mobile device equipped with a camera to take video or still pictures in order to capture the real-world environment of a plurality of hospital rooms with a plurality of patients undergoing in-patient care within the aforementioned hospital rooms. The captured images recognize tagged and untagged objects within a hospital room. The relative distances between the tags are calculated. Thus, the image along with the aforementioned set of distances and other information is input to the analytics module of a hospital decision information system.

The analytics module determines whether the captured environment of the patient adheres to regulatory and operating protocols. Based on the results which are output from the analytics module, augmented and annotative information are fed back to the mobile device. The mobile device may run software applications that may interpret the aforementioned information to overlay the images of the real-world observed by the user either with text-based instructions or graphic overlay of the hospital room environment indicating deviations from the protocol if any.

The analytics module extracts the patient's ID and associated electronic medical record (EMR), electronic health record (HER), and HIPAA associated information restrictions from the patient's identity tag. The module outputs a procedure, a set of rules, or steps for gathering relevant data about the patient, embodied as a form, questionnaire or a set of required parameters, and delivers the information request in an interactive user interface on a mobile device. The aforementioned embodiments are not exhaustive. This information is relayed back to the mobile device which may be mounted by the hospital, lent by the hospital, or may be the property of an individual. The form or questionnaire with a set of parameters is structured to allow the patient to retain his/her privacy while providing data, according to standard regulatory or hospital operating policies.

In one embodiment, the patient data is collected by a hospital care provider doing rounds. The hospital care provider may vary in range of skill, since the augmented information is complete and detailed enough for a person of limited skill in hospital care to successfully gather specific and critical care information about the patient's state and condition, as well as the patient's perceived well-being, and other unstructured information.

In another aspect of the invention, a system and method is provided to the patient or patient family members or patient advocates to access the hospital operational decision support system from their personal mobile devices for the purpose of providing perceived well-being, patient status, and receiving information from the hospital operational decision support system pertaining to and including, but not limited to, next steps in in-patient care, discharge information, patient food consumption and exercise, location, recording rounding and other directed aspects of care delivery. The patient or patient advocate or patient's kith or kin may be provided access and login privileges to the hospital operational decision support application at the time of admission. The application provides a means of displaying the next steps in treatment, work flow and actionable instructions to the user. Further, the application provides means for the user to input the status of the patient, the patients' perceived well-being, patient's food consumption and exercise sessions. The application also provides means for displaying the hospital menus, next round estimated time, exercise time, discharge information and other directed aspects of health care delivery to the patient. Such means of the aforementioned includes visual/audio capture by a personal mobile device or authorized hospital device or system. Thus, the means may be a camera, microphone, webcam, an interactive social media site, or video application for easy access and data sharing within the secured network.

An embodiment of the invention, for exemplary purposes and not limitation, utilizes an iPad® prototype which includes as an exemplary embodiment, a software development kit (SDK) from Qualcomm® that provides the image and tag identification functionality for mobile devices (iOS and Android), such as through the website: https://www.vuforia.com/. Tags are placed on wrist bracelets of patients, badges of care providers, medical equipment, trays, clinical supplies, bed components, rooms, location, and sundry items in hospitals. The device is carried by a person doing rounds in a hospital. The camera points at the bed area and captures patient ID, bed ID, room ID, supply ID, and device ID in the vicinity. The relative locations of tags are calculated. A determination of adherence to operating protocol is made, such as when bed rails are raised, bed height is low, or tray items are too close for fall risk patients. Based upon the patient ID, the patient name and several questions are given to the person doing the rounding. The questions include prompting for missing equipment, information as to patient state or condition, and other structured data inputs as predetermined by the IT management systems. An example input would be a graphical user interface with a happy face and a sad face which the person making rounds would select to characterize the patient's overall state. The mobile device screen displays: (a) "red" for setups out of compliance and (b) "green" as specific parameters in compliance.

An embodiment of an information acquisition system (IAS) 100 is illustrated in FIG. 1. As situated in a hospital setting, system 100 integrates broad dedicated networks whose edge devices may be hard wired into a physical plant (not depicted). Edge devices enable analytics and knowledge generation to occur at the source of data. The approach leverages connected networks and devices connected thereto such as laptops, smartphones, tablets, and sensors (e.g. wireless sensor networks), mobile data acquisition, mobile signature analysis, cooperative peer-to-peer networking, and cloud computing, among others, and based on current definitions. Referring to FIG. 1, a system 100 is designated in a planned hospital setting. The system 100 typically provides for designated geo-locations such as rooms 105 where clinical activity is conducted. Other networked space includes information technology (IT) locations 110 for computing and communications assets 135, including but not limited to, any information technology and physically connected hardware or mobile networking. As depicted, a connected network 115 communicates with sensing or communications devices 120 which may be a designated entity or a hub in a location for the further connection of a physical asset 125. The physical asset 125 may be a terminal or clinical device or a location detecting device 130 such as Radio Frequency Identification Device (RFID) station. Local computing assets 135 can also be connected either as integrated components of hospital operations, medical care delivery systems, or as computers with processors that may, in part, be used by the disclosed system for display and/or computation Other networks such as wireless (Wi-Fi) allow an electronic device to exchange data or connect to the internet wirelessly using radio waves and rely on localized hubs 140 with connections 145 back to on-premise communications assets 135. Public networks such as cellular 150 are utilized to minimize expense and provide internet connection for broad intercommunication. Specifically, cell tower connections 155 to telecommunications computing assets 165 in healthcare provider facilities 160 connect to the internet 170, which enables communication with hospital nodes 175.

Hospital networks such as Wi-Fi®, with fixed capital expense to install, are comparatively lower cost than dedicated networks for data acquisition, such as RFID. Additionally, their use is amortized over multiple activities such as computer connection for guests, mobile device connectivity for Electronic Medical Record (EMR) inputs, processing, analytics, and outputs. One of the lowest costs to a hospital is a network it does not itself own or maintain, such as a cellular network. Cellular networks have external transceivers outside the hospital or are integrated into the hospital network.

Figure 2:
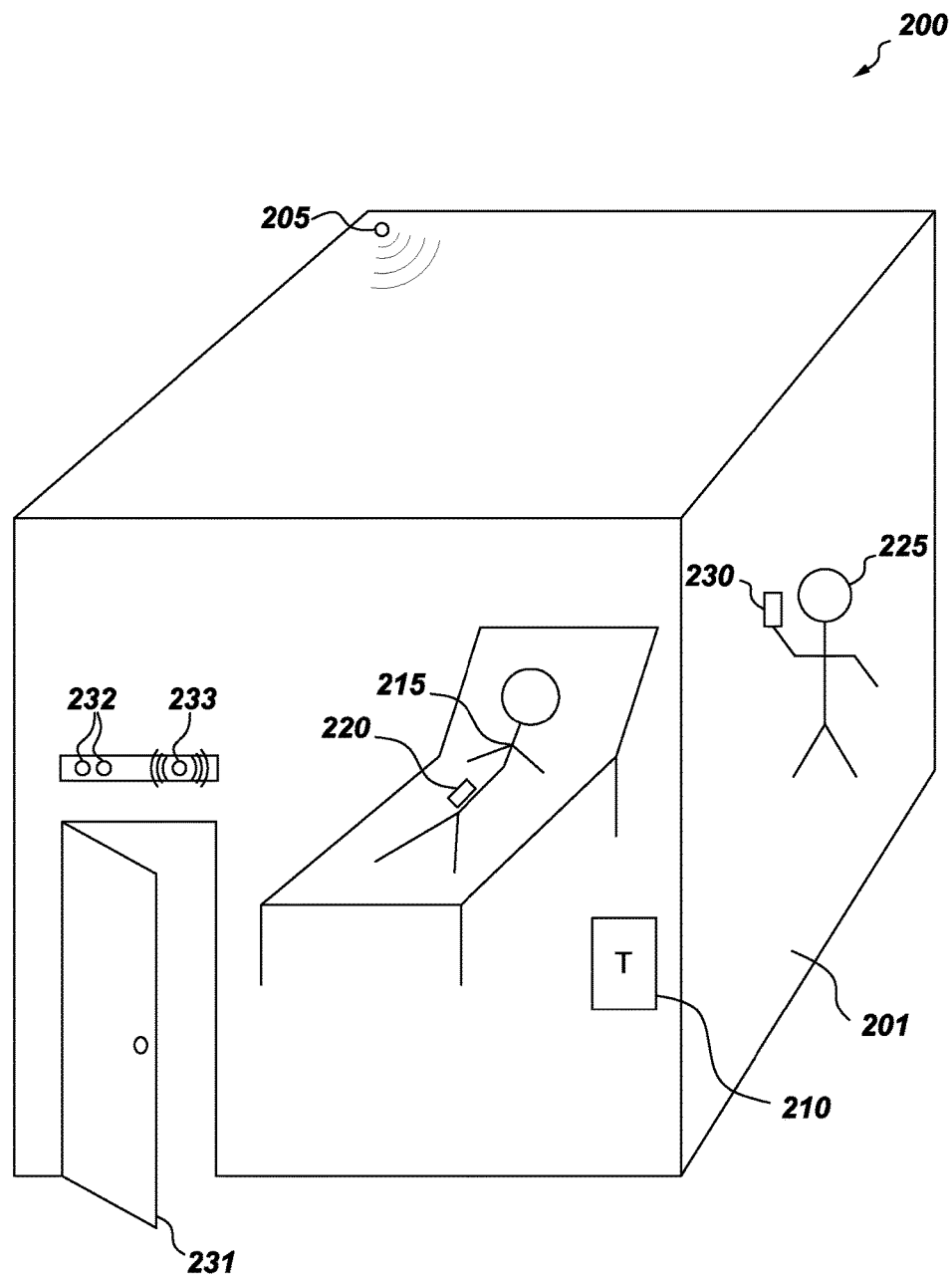
FIG. 2 depicts an embodiment using wireless devices in a patient's room.

Referring to FIG. 2, a system 200 is integrated in a hospital room 201 with an RFID station 205 and a terminal 210 installed. For exemplary purposes, and not limitation, two persons, a patient 215 and a visitor 225 are networked into the system. The patient 215 wears an active RFID tag 220 which broadcasts its identifier and its location is resolved with the station 205 singularly and in concert with other stations outside the room 201. The visitor 225 has a mobile device 230 such as an iPhone™ with an embedded camera and edge computing capability. On the mobile device 230 is software that is downloaded at no cost to the visitor 225 or to the patient 220. The terminal 210 communicates on the hospital's Wi-Fi network or cellular system. The system disclosed uses the mobile device 230 to locate the patient in geo-location, rather than use the more expensive dedicated network or Wi-Fi networks.

In one aspect, the room 201 provides an external alert 232 and speaker system 232 near the entry or door 231 to the room. The alert and/or speaker system is to notify care providers external to the room as to patient condition or support as to protocols and continuous monitoring. Thus, the alerts and/or speaker system may be placed anywhere that provides visibility, easy viewing or unhindered audio from the speaker.

Figure 3:
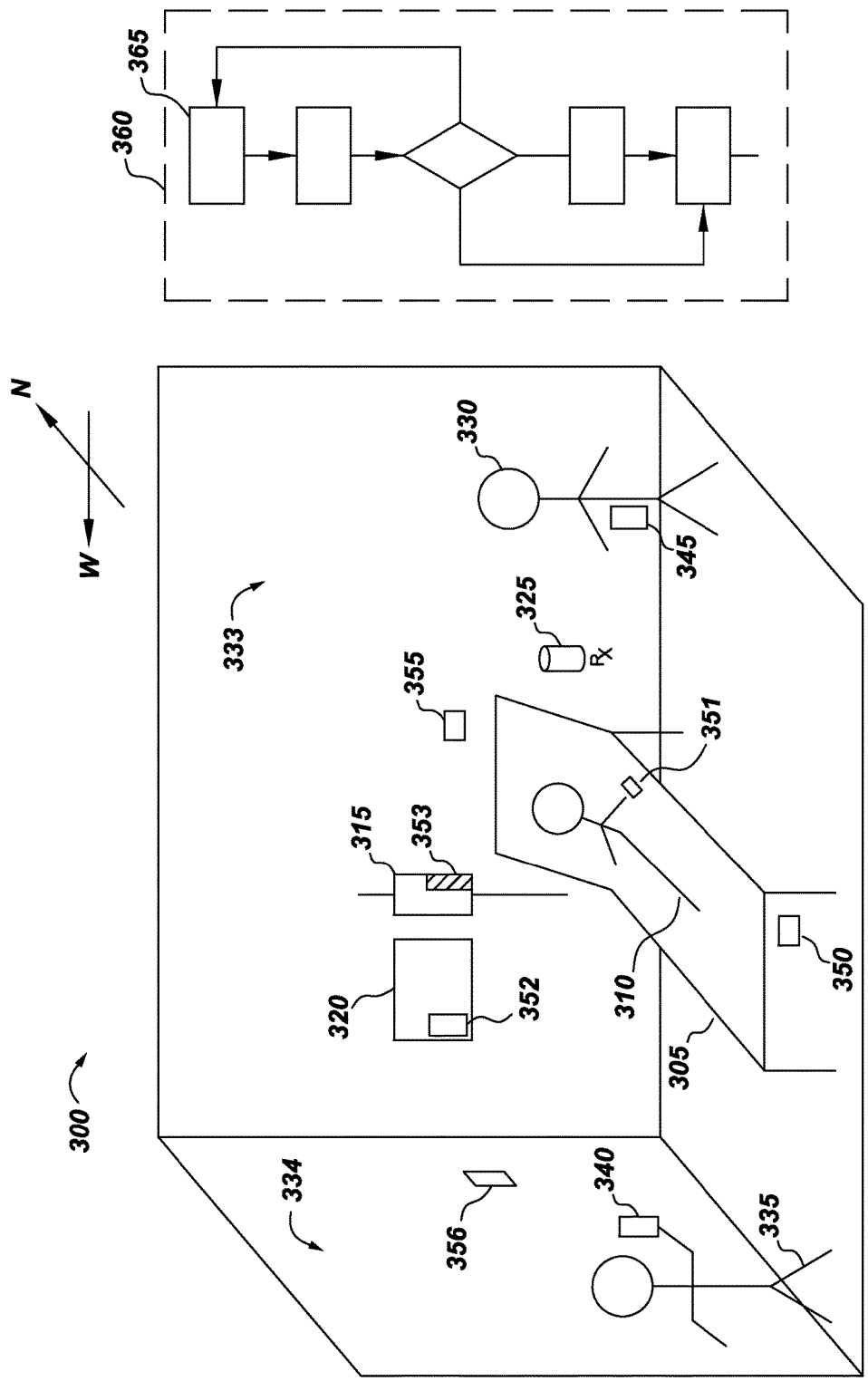
FIG. 3 depicts one embodiment of a system integrating people, assets, location, and processes.

One embodiment in a care environment has many assets and persons who are stakeholders in a patient's care plan. Stakeholders include clinicians or healthcare providers, physicians, care staff, service staff, and agents within the care facility, including a visitor of the patient. Stakeholders also include family or friends who have an interest in the patient's care or treatment plan. Referring to FIG. 3, a patient room 300 has a bed 305 which may be moved about the room and also used as a transportation mechanism to other locations such as, for example, the perioperative environment or diagnostic imaging. The patient 310 is located on the bed 305 as depicted, yet is not confined to the bed 305. Also in the room 300 are clinical devices such as an intravenous (IV) system 315 with a fluid filled bag and a clinical device 320 such as a SpO$_2$ or pressure ulcer prevention sock or bed pad. Prescribed medications 325 are made available according to the clinical protocol 360 for the patient 310. A care provider 330 such as a nurse, orderly or doctor have an identification tag 345 that is embossed with a pattern discernable by commercial grade mobile devices such as cell phones with cameras 340 held by a visitor 335. Also tagged with an optical pattern is the patient's bed 305 via a uniquely patterned surface 350, the patient 310 with optical tag 351, and the individual walls 333 and 334 of the room 300 with optical tags 355 and 356, respectively. The optical tags 345, 350, 351, 352, 353 and 355 are unique. The tags may be affixed to other locations and identification devices such as a name tag or even an RFID.

The bed 305 is associated with an affixed tag 350. Clinical devices 315 and 320 are associated with tags 353 and 352, respectively. The north wall 333 of the room 300 is associated with tag 355, the western wall 334 with tag 356. Tags 355 and 356 are at registered locations on their respective walls. Images with both tags in them enable a location inference of the picture source, such as from mobile device 340 and derivation of other assets such as the IV 315 or bed 305 orientation. The patient 310 is associated with bed 350, devices 320 and 315 and medication/dose 325.

In one embodiment, optical tags are low cost material with printed or embossed patterns. The tags are attached to surfaces with permanent or temporary adhesives or loop felt. The optical tags also in one embodiment are integrated in the structure or the surface of equipment or furniture, such that the tags can easily be removed and replaced.

The IV 315 meters fluid. In one embodiment, the optical tag 353 is a series of patterns or discrete tags. The IV 315 level is inferred via the tag(s) 353 exposed, such as in the background of the fluid.

The presence of the care provider 330 is determined by the visitor's 335 snap of an image on device 340. The state of the patient 310 being in room 300 by the tags 355 and 356 are in the frame with tag 351. The patient 310 is in bed 350 as established by association of patient tag 351 and bed tag 350.

A clinical protocol 360 is a sequence of tasks 365. An example protocol prescribes a medication 325 be provided to patient 310 to be delivered by care provider 330 during a given time duration. The disclosed system 300 monitors for protocol steps 360 and provides adaptive workflow 365 in response to the state of the care delivery. Protocol may include any number of medical treatment options, testing, prescription of medication, direction for communication or interaction, as well as timing for procedures, blood withdrawal, intravenous injection, blood pressure reading, pulse, retinal scan, among others.

In one aspect, the patient 310 has a care plan or protocol 360 that includes rounds of a care provider 330 so many times per day (e.g. three times per day). The system 300 monitors for rounding of provider 330 in room 300 to see patient 310. Prior to discharge, the patient's stay is replayed such that the prescribed protocol 360 with rounding is shown in a graphic schematic or full replay video as to when the care provider 330 did actual rounds. Aspects of the recorded replay include duration of the care provider visit during rounds and specific logged activities. The patient's understanding of the prescribed protocol and what actually happened is made more accurate and easier to recall later when the patient satisfaction survey is conducted some days or weeks after discharge.

Figure 4:
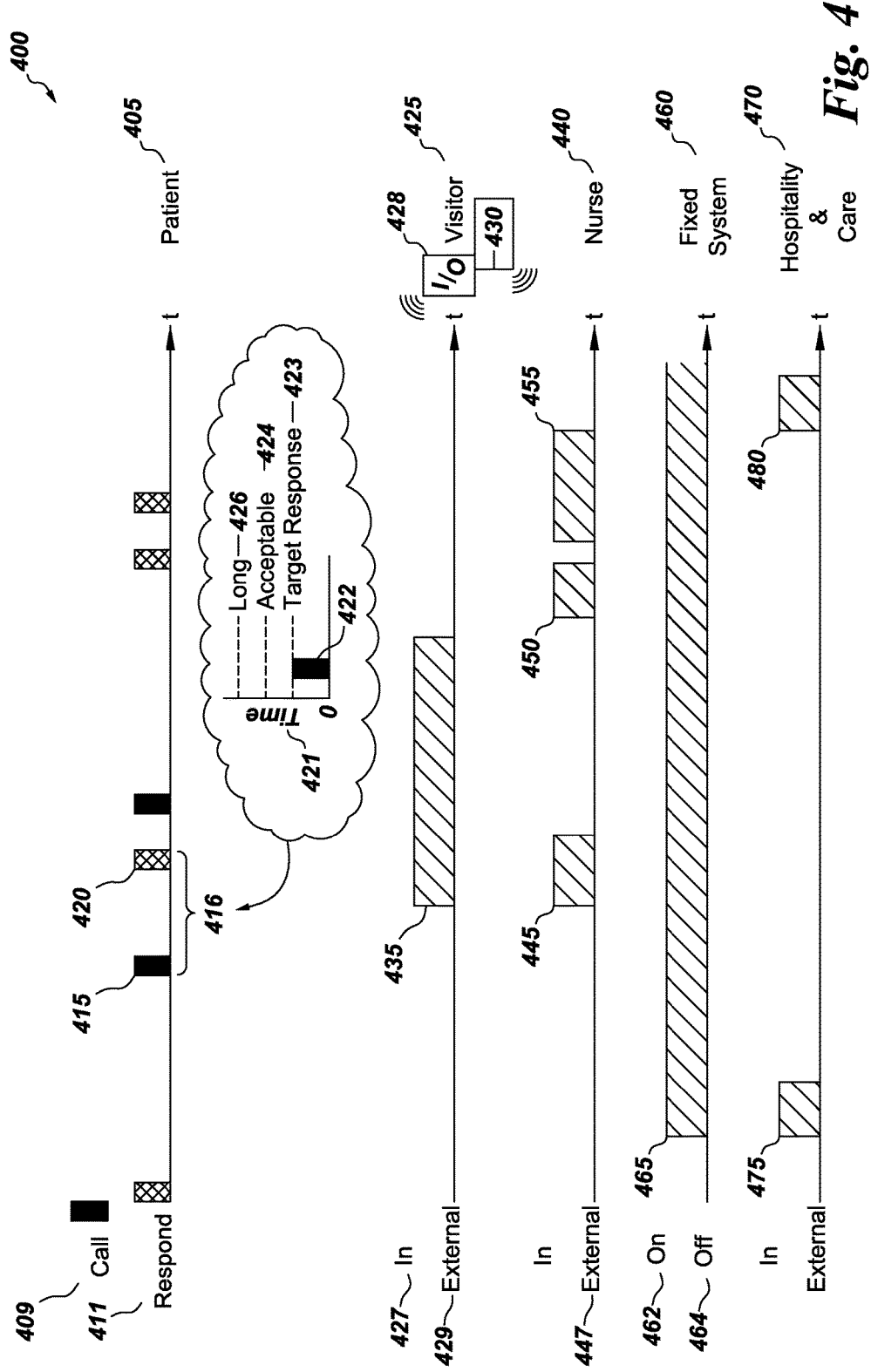
FIG. 4 depicts an embodiment of the system using time of presence in characterizing the patient environment.

Referring to FIG. 4, a timeline 400 of stakeholders includes patient 405, visitor 425, care provider or nurse 440, fixed system 460, and hospitality and care personnel 470. Each stakeholder's activity with respect to being in the environment is connoted on a time axis 407. When the patient 405 desires a care provider 440, the patient presses the call button 415 to activate the nurse call system 409 which is subsequently responded to via the response system 411. The elapsed time to respond 416 is determined as the duration between nurse call 415 and entry of the nurse response 420. In another aspect, the call 415 may be for another care stakeholder and may be registered with a nurse call system or via connected text or smartphone applications. As depicted, the care provider 440 was present in patient location for a duration 445. The elapsed time 416 between call 415 and response 420 is an indicator for staffing capacity to be used in post process analysis in conjunction with staffing decision support. The fixed and average (fixed or moving) time 416 is categorized on axis 421 as duration 422. A duration less than the target duration 423 indicates a satisfactory response for the specific call event. The duration that is set as the target 423 is determined by observation or judgment. The duration may also be attained by correlating highly rated patient experiences with observed durations.

In another embodiment, the target response 423 is a control variable in a numerical simulation of the hospital care delivery process. In the simulation, patients are given frequency of calls logic calibrated to observed (real-world) patients (See FIGS. 7, 8, 9). Hospital simulated staff are added into the numerical simulation of the hospital operation and given a cost. Various staff types have different salaries and qualifications. The cost of serving to meet the target response time with the appropriate skilled staff is then compared to response time and correlated to patient satisfaction scores, and controlled for patient descriptive attributes. Further still, the cost of staffing either determined via numerical simulation or with the observations the disclosed system provides, the system enables comparison to the incentive revenues available in pay-for-performance type reimbursement structures. Staff is added to the aid the rate of return established by hospital management.

Figure 8:
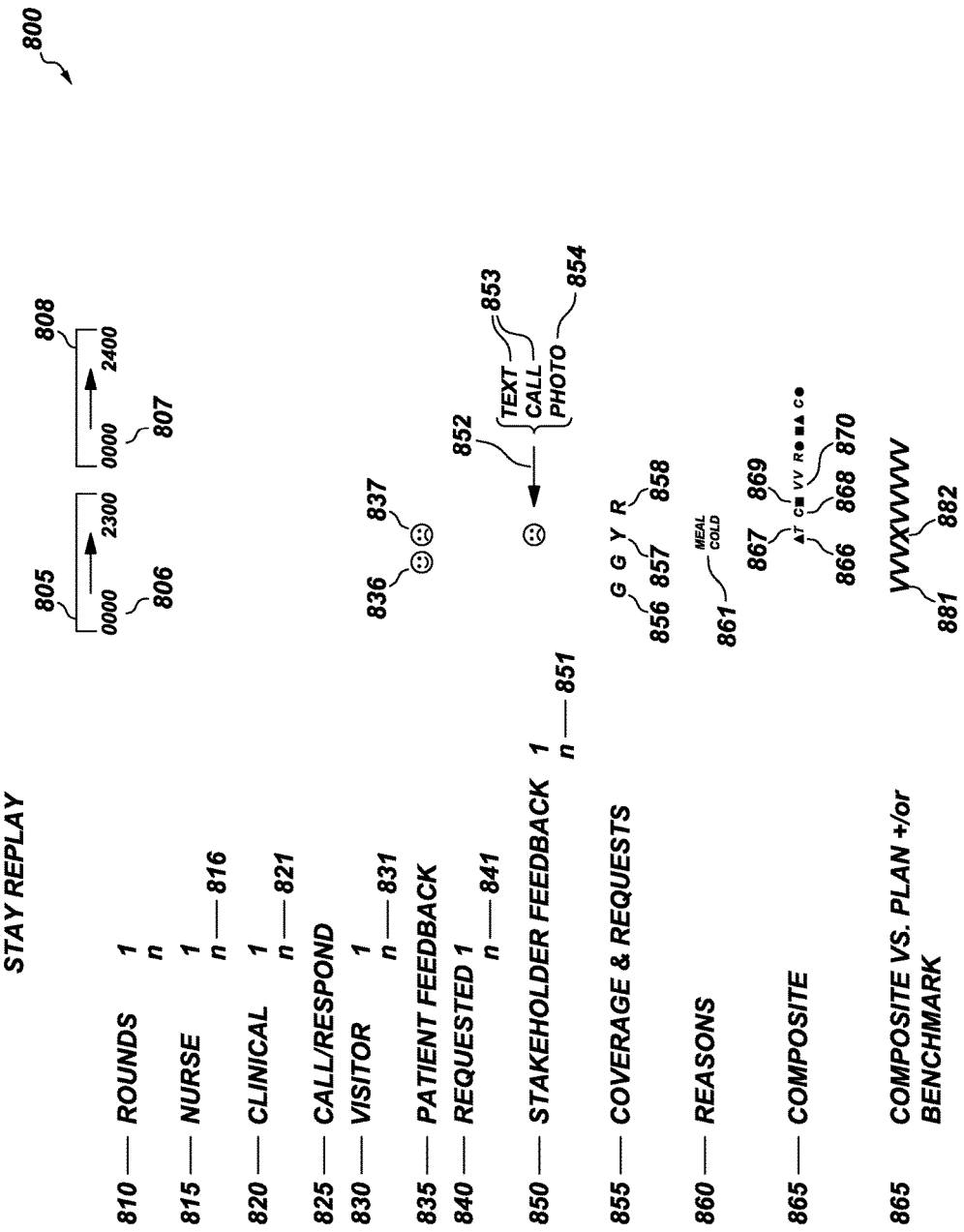
FIG. 8 illustrates an embodiment that incorporates stay replay.

In the embodiment of FIG. 4, an acceptable response duration, or threshold 424 is established by policy or the method previously disclosed. The threshold point 424 is dynamically adjusted as information learned about the target patient (See FIGS. 8, 9) such that the durations 416 for various patients 405 are a function of personality, descriptive attributes, staff, and visitors. As shown in FIG. 8, patient feedback 825, both positive 836 and negative 837, if determined to be a function of any other monitored attribute, is used to adjust the acceptable time to respond 424.

The duration 416 on a time plot 421 is deemed "long" 426 as established by the disclosed method previously described or by judgment. The duration is acceptable 424 or at the target response time 423 as designated in the plot.

A visitor 425 is in the room 427 or associated in the same geolocation 427 as the patient 435. The visitor 425 may not be with the patient and an external location 429. The visitor 425 with a registered mobile device 428 is in communication with the disclosed system's logic. The visitor 425 may not have a mobile device but rather communication support 430 in connectivity with the hospital infrastructure through the system's designed software application. The disclosed system uses attributes of visitor 425 to promulgate care prompts if other care stakeholders or nurse 440 are not available, or external 447 to the environment.

The nurse, as a proxy for care providers 440 is with the patient 405 at times 445, 450, and 455. This information is used by the disclosed systems communicator logic to engage other stakeholders such as registered visitor 425 or lower skilled hospitality and care providers 470. The location data is attained by RFID, locating data from mobile devices or association data gathered by visitors with registered devices 428 who are present in the environment. The data is also used to build assumptions for numerical simulation of the care delivery process.

A fixed monitoring system 460 such as RFID or camera based device is typically always available and "on" 462. This fixed monitoring modality, if installed, is used to validate inputs from mobile devices Hospitality and lower skilled care providers 470 may be rounding, scheduled, or called to a location 475 or 480 by the system. The system 400 checks for location of patient 405, registered visitor 425, nurse 440, hospitality and care providers 470, and other tracked stakeholders and equipment. Assignment logic is described as "delivery of healthcare protocols in day view form" versus publication. In the example of FIG. 4, a nurse call 415 is first responded to by visitor 425 in the room 427 using an activated mobile device 428. On the visitor's mobile device 428, the disclosed system asked for, as an example, patient's pain level and request, categorized by "medication", "toileting", "drink/meal/snack", "clinical question", among any number of potential categories. The disclosed system provides the visitor 425 instructions, some of which are graphically superimposed onto the mobile device, overlaying a picture that visitor 425 submitted, or an exemplar graphic.

Figure 5:
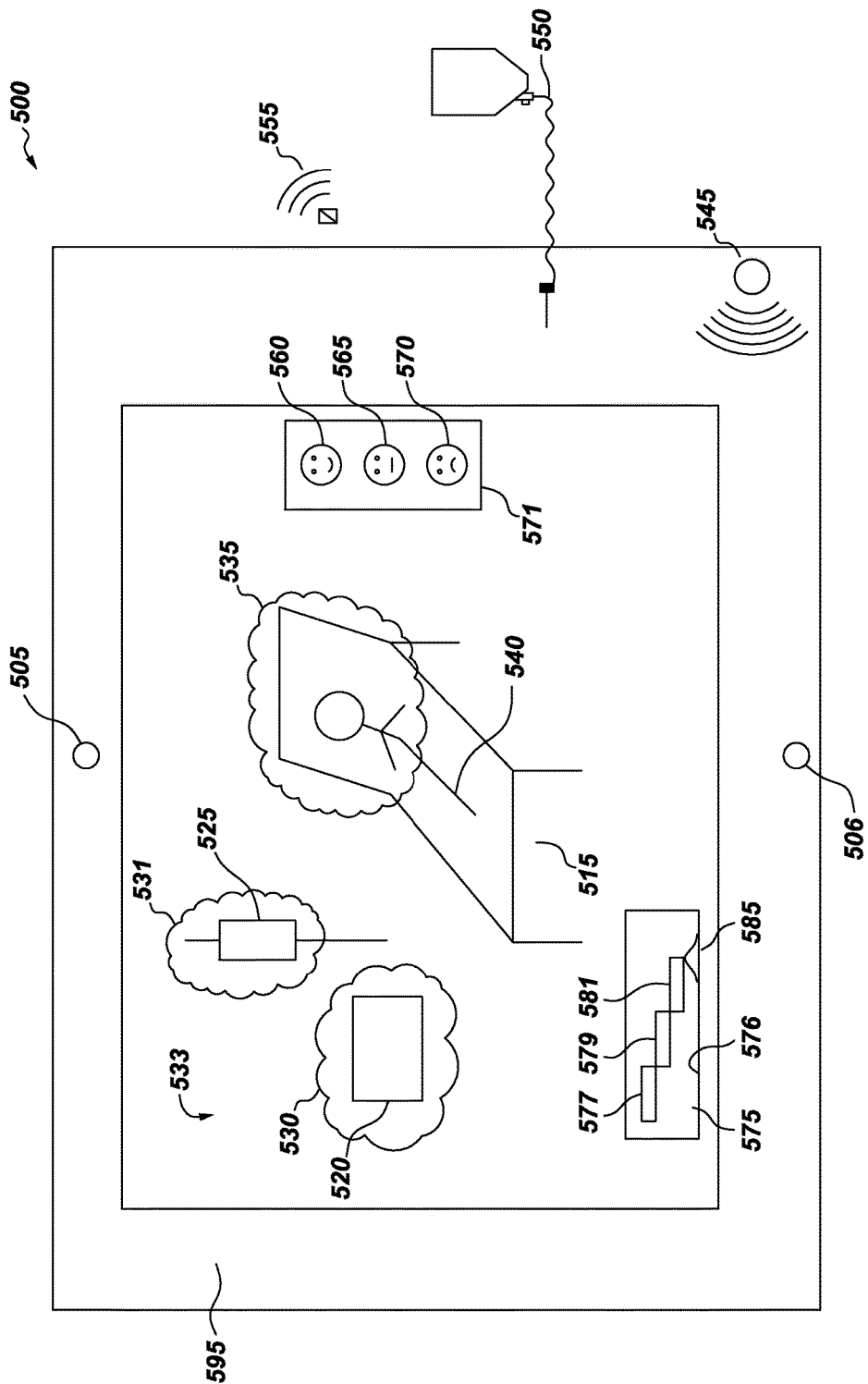
FIG. 5 illustrates an interactive visual input/output (I/O) device with directed data and process superposition, in accordance with one embodiment.

In one embodiment, the disclosed system integrates with the care environment, patients and care stakeholders in an interactive optically based means. Referring to FIG. 5, a mobile device such as a smartphone, tablet, or iPAD® with an ability to download applications, connects via Wi-Fi® and/or cellular network, and has the capability to take a picture as well as to receive and display a graphic. In FIG. 5, the mobile device 500 is employed to guide care stakeholders in delivery of care protocols, receive instructions, and gather data.

In an example embodiment, a tablet mobile device 500 with camera 505, sound input 506, speaker 545, audiojack 550, screen 595, and connectivity 555 to a cellular network and/or Wi-Fi is used. Further, in the example embodiment, the screen 595 is interactive. A user, such as a visitor 425 downloads the application and registers the device and user. A picture of a patient's room is captured and sent to the disclosed system's server(s). In the transmitted image is a patient 540, bed 515, IV 525, other clinical system(s) 520 and associated optical tags.

The optical tags are reasoned over to associate a unique identifier. The tags are on equipment such as the IV 525, bed 515, patient 540, and wall 533 of the room. A logical association is made between patient, bed, room, and clinical apparatus to establish location via optical characters recorded and computed over.

Various aids 510 are returned to the tablet device 500 via wireless communication 555 for the care stakeholder(s) view. The care stakeholder, for example, is a visitor 425 or hospitality or care person 470. Example aids to the care process are a patient overall indicator 571, connotations such as "ok" 560, "indifferent" 565, or "unhappy/not ok" 570. The care stakeholder presses the appropriate icon (e.g. 560, 565, 570). The patient status 571 box changes color indicating data received and an audio signal is sent.

Also, returning to the tablet device 500 are process indicators. The care stakeholder is provided instruction in graphical, text, and/or audio form. For example, a request to recheck location is highlighted 530, IV bag with a highlight 531, and patient bed angle setting or rails position 535. When the requested data (e.g. 530, 531, 535) is entered, or when a new picture is sent with the requested adjustments verified by the disclosed system, the attention highlights 530, 531, 535 fade out. The highlights may be clicked for more detail or directly connect to a human care technician who interacts with the stakeholder via the mobile device 500.

Further, the tablet device 500 comprises process indicators. Clinical workflow 575 is indicated by three tasks 577, 579, 581 in an exemplary protocol. Without limitation, any number of tasks may be included in the workflow. Tasks may have interdependencies, the logic of which may include constraints-based programming or multi-resource scheduling. The event task 581, for example, is a radiological exam for which the patient is given a contrast agent in the first step 577, transported 579, and then given the exam 581. The timeline 576 provides an indication of duration from the present or as clock time, individually or in combination. A variation in schedule is indicated 585 as a likelihood and is provided to the care stakeholder for communication to the patient to manage expectations.

Further, in embodiments of the system, hospital infrastructure integrates surveys to ascertain how patients perceive care quality received during their hospitalization or during interaction with healthcare services in clinics, standard units, rehabilitation centers, and patient homes. The patient is able to take the survey from home or at discharge from the facility as to their basic care, treatment, contact time with healthcare providers, and quality of care. Surveys may be direct or given by a care provider or administered via a third party. Surveys may occur during the care duration at the healthcare provider's facilities or afterwards, such as days or weeks after discharge. Surveys may be electronic, paper based or interview based either by phone or in person. Surveys may be structured and fixed or adaptive depending upon responses. The scoring and characterization of surveys on a comparative basis typically results in statistical comparisons along quality of care aspects, trending over time and amongst other businesses such as regional alternatives, specific competitors and national piers by selected descriptive attribute.

The aims of such surveys typically are to improve the care quality of the operation, to competitively differentiate an institution and to raise financial vitality via that differentiation as well as enhance performance based revenues. The invention is a method and system to attain these aims.

Figure 6:
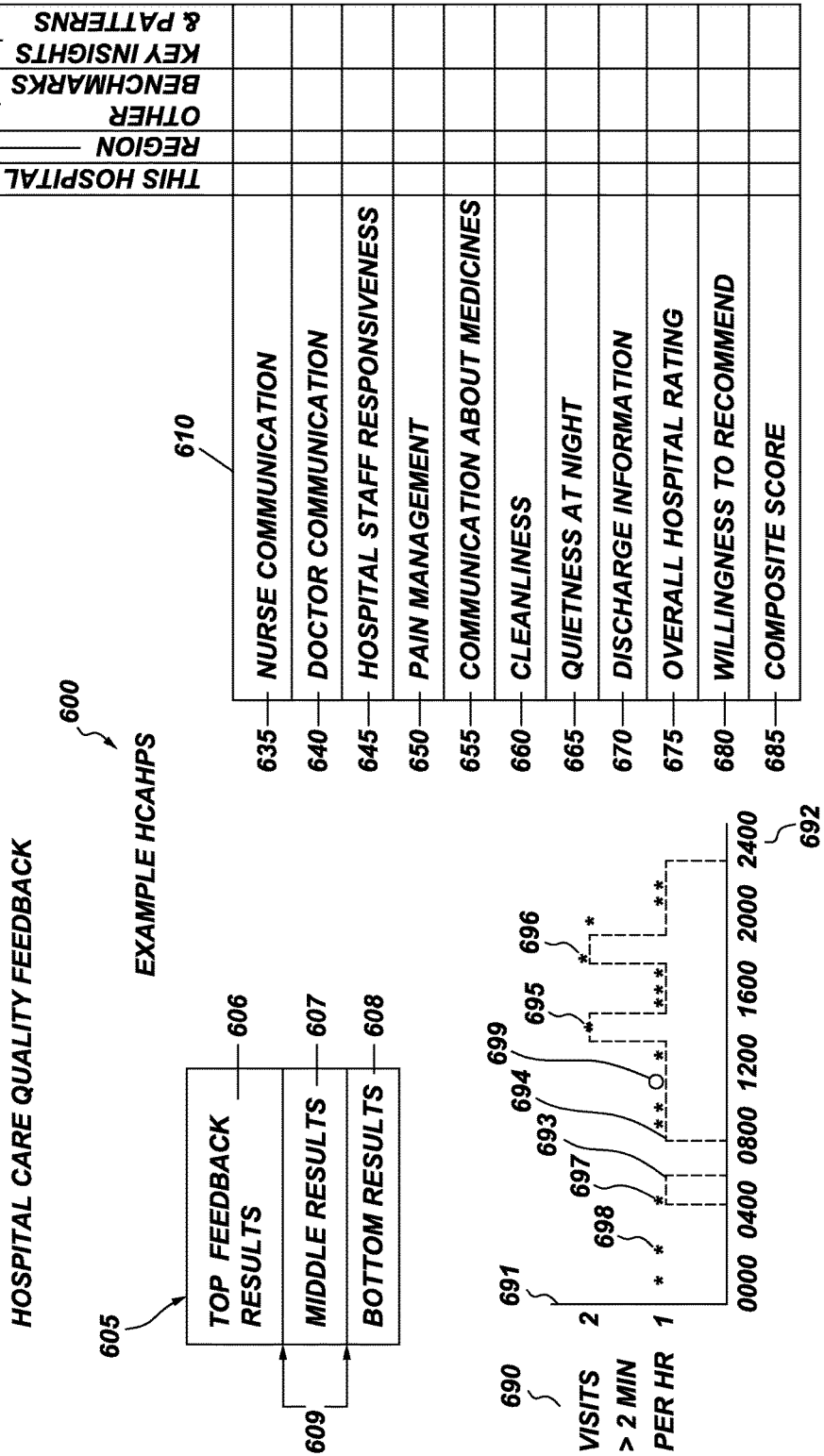
FIG. 6 illustrates an embodiment of the system with hospital care quality feedback.

Referring to FIG. 6, aspects of a hospital care quality feedback system 600 are described. A survey is used where measures describe an institution's care quality performance, with the intention to raise the care quality as measured by survey.

Differentiation may be indicated by clustering results into contents of rank or similarity. One such clustering and ranking is a structure 605 of top score feedback 606, middle result 607 and bottom result 608. It can be appreciated that there may be any number of classifications and clusters with criteria thresholds 609 predetermined.

Critical quality aspects 610 are used for assessing the subject hospital institutions 615 or regional institutions 620 such as those in a geography or a certain one or more competitive alternatives to the subject institution, such as national or international best in class 625. Comments, clarifications, insights or summary observations, and qualifications 630 are also added.

The specific categories which determine clinical quality may be, for example, nurse communication 635, doctor communication 640, hospital staff responsiveness 645, pain management 650, communication 655, cleanliness 660, quiet at night 665, discharge instruction 670, overall hospital rating 675, willingness to recommend 680, and composite score 685. The invention encourages the hospital, patients, visitors, care providers, staff and administration to improve upon one or more aspects 610.

The disclosed system enables communication performance improvement on two dimensions: (1) The specific ability to measure with higher fidelity is enabled when, for example, a nurse visits with a patient in terms of frequency, timing, and duration; and (2) The system replays the patient's stay for the patient and their care stakeholders to achieve and recall actual events and specifics in reference to those events. The two dimensions address active time with patient, preferably per an institution's protocol, and establish firmly in the patient's mind that communication did in fact occur.

For exemplary purposes only, and not limitation, in one embodiment a rule is set including the number of nurse visits per specific hour of the twenty four hours in a day and the duration of in-room visits. The protocol may include a consultation before and one after a care event or a patient query. The system enables collection of care stakeholder visits and compares the visits to a protocol whose values are determined by correlation of survey responses to descriptive attributes of patients.

The embodiments of the invention address aspects of surveys to prevent a patient's lack of context or recall with respect to delivered services in comparison with those planned. For example, a survey question to the effect of "nurses were present to explain my care and assess by condition" may solicit a neutral rating because the respondent was not aware or could not remember how often nurses were in contact. Firstly, the invention "replays the stay" prior to discharge and compares frequency satisfactory duration to protocol. The intent is to assess care provided and anchor the patient in facts so that when responding to a later survey, the patient will better recall the care actually provided. A third benefit is to enable workflow reminders during a shift if protocols are not going to be met. The system sets a notice to bed boards, mobile devices, or triggers indicator lights if a visit or a duration of a visit has not been met.

To illustrate, the protocol visits and duration 690 are set for each hour 692. A check-in may not be required for the first hour, for example, between 0400 hours (693) and 0800 hours (694). Due to historical experience or because of certain processes or events, two visits are required 695: A nurse is called for a single visit within the hour, for example at 1900 hours where the protocol is one visit. Yet, due to a nurse call, two visits were needed and the nurse responded 696. Nurse visits that met duration requirements 690 are recorded (as marked by "*"). For example, during the 0400 hours, a single visit of two minutes or greater is required by a determined protocol 693, along with an occurrence 697. An extra visit(s) is recorded 698. A missed visit (designated "o"), such as at 1000 hours 699 is likewise indicated and alarmed with a set point, for example, at 50 minutes in a 60 minute period for reminding the particular care provider.

Prior to a patient's discharge, the patient's stay is replayed for the patient where the responsiveness of staff is shown within the established limit and protocol of "good care". Where the responses did not occur in time, a reason may be provided or another lower skill, lower cost hospital staff person arrives in order to establish contact and respond to concerns. The system provides the visitor 425 with questions to ask the patient or tasks to perform in a graphical way with decision support superimposed onto the graphical layout of the patient, bed, room and overall captured aspects of the environment.

A beneficial aspect of the disclosed invention is the engagement of stakeholders in the processes of care delivery. The barrier to engage the stakeholder visitor is lowered where the stakeholder has a mobile device capable of downloading an application and following basic instructions delivered via the mobile device.

Figure 7:
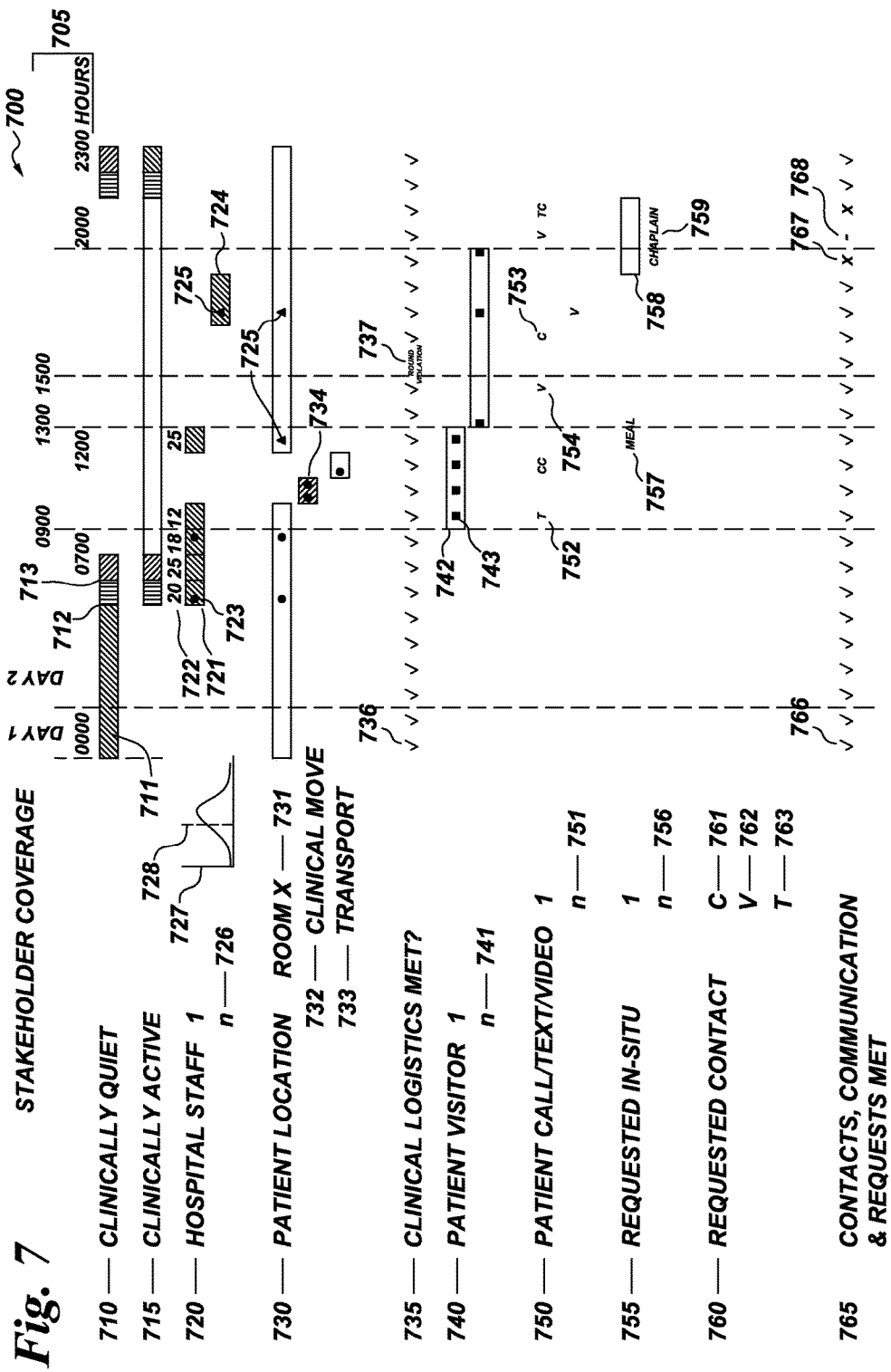
FIG. 7 depicts stakeholder coverage in accordance with one embodiment.

A method and system to manage stakeholder coverage of the system 700 is provided and depicted in FIG. 7.

In one embodiment, a 24 hour time sequence is used to describe how the coverage of patient care delivery is monitored and reported. It can be appreciated that other durations than a 24 hour cycle can be used, such as 8, 12, 16, 48, 60 hours, among other variations of time and data collection. Time durations in minutes, hours, or days, for example, may allow data extrapolation as desired by a user. For illustration, the duration is the planning period.

One embodiment of the integrated hospital system 700 as used for clinical decision support encompasses a planning period 705. Various aspects of clinical activity and stakeholder involvement as to health care provided and protocol delivery processes are monitored and reported out. Therefore, managing schedules is desirable. The disclosed invention provides the means to schedule stakeholders to monitor and assist delivering care with the use of mobile devices and applications. The system and method of the invention also allows stakeholders to schedule, monitor, and assist in the delivery of care to patients using mobile devices and applications secured to the hospital infrastructure.

Typically in planning, periods of a day cycle that are clinically quiet periods 710 demand little patient interaction, such as when the patient is resting or sleeping. Such a period may extend from 2200 hours one day to 0700 hours the following day. During this clinically quiet time, as an example, stages of sleep with different degrees of sleep quality have proven beneficial medical effects. The disclosed invention allows discrimination between different times of a class of coverage period. For example, during a clinically quiet period 710, when the patient is sleeping, a period of transition occurs from deeper sleep 711 to transitory period 712 and again from transitory period 712 to waking 713. During the transitory states, monitoring or care delivery changes may be desired, and therefore certain care stakeholders such as hospital staff 720 or patient visitors 740 may be scheduled for coverage. Depending upon the stakeholder, such as a visitor 740, using a mobile device to participate in monitoring and directed care delivery, the scheduled care can be modified. In this aspect, patient coverage and care changes are mapped to sleep patterns.

As the patient emerges from deeper sleep 711, a threshold is met where depending upon desired stakeholder coverage as specified in a care plan, a certain care stakeholder, such as hospital staff 720, is employed for monitoring or care. Transitory period 712 between clinically quiet 710 and clinically active 715 utilizes hospital staff 720 in the illustrated example from 0500 hours to 0600 hours. Yet, a probability distribution 727 with a threshold 728 determines how a stakeholder can serve one or more patients. Lower probability demand, to the left of the threshold 728 in a probability distribution 727 demonstrates the likelihood of needing a stakeholder such that the covering stakeholder may be able to serve several patients. A plurality of care stakeholders enables a change in the ratio of hospital staff to patients. The skills of various hospital staff are also practically allocated, such that a medical doctor coverage ratio is different from that of a nurse. Likewise, a nurse coverage ratio is different from that of an aid. The ratios of skills and appropriated staff are tracked ratios 722 and used to trigger hospital operations and alerts when a threshold is reached. As demonstrated by the ratios 722, patient to nurse ratios, respectively, are 20:1, 25:1, 18:1, 12:1, and so forth, as designated by hospital operations.

Hospital staff coverage 720 is scheduled at time period 721. A particular staff 720, when tending to a patient, is recorded as an event 723 while other staff 726 who are scheduled at a later time period 724 are recorded as being with the patient at time 725. Symbols for staff or types of staff, and their respective roles, are recorded. Multiple staff are scheduled, here shown as two hospital staff, as represented by time periods 721, 724.

An aspect of monitoring and providing directed care is having coverage where the patient is at a location 730, which may typically be a room 731. As the patient prepares for a clinical move or transition, the pre-operation 732 is tracked as well as enroute transport 733. Care stakeholder interactions occur and are recorded for outcomes analysis and patient satisfaction decision support. The likelihood of actual clinical activity, care delivery, and thus monitoring is different depending upon a patient's condition and personalized clinical activity scheduled. Blocks of time 734 are thus marked and designated with levels of probability, the probability that a patient needs monitoring or delivered medical care.

Clinical staff coverage and the corresponding patient care plan are tracked in a clinical logistic system 735. In an exemplary embodiment, a clinical care system is designed for patient interaction such that the system pre-sets a plan for the patient not to be interrupted between 2300 hours and 0600 hours (711), where the system is located in the room 731 and does not have hospital staff coverage. For example, from 2300 hours to 0600 hours, the clinical logistics were met, as designated 736. As a further example, at 0700 hours, nursing supervision is specified and is met by a nurse being scheduled with a patient to nurse ratio 722 within a particular location. Further, at 1500 hours, a clinical round with patient contact was not made for 6 hours (since 0900 hours). If, by example, a protocol for one touch per every four hours is not realized, a rounding violation 737 is be recorded. It is appreciated that alerts to avoid such care protocol defects are provided by the disclosed system to a nurse call system, to room alarms, and to other devices with mechanisms to facilitate hospital staffing operations management.

In the disclosed invention, care stakeholders such as family and friends facilitate the monitoring, care delivery and patient satisfaction process. One aspect is the ability of patient visitors 740 to schedule time with the patient such that any number of visitors 751 may be monitored. Visitor number '1' in the example embodiment is covering time period 742 from 0900 hours to 1300 hours during which time four interactions are registered 743. A second visitor 'n' provides coverage from 1300 hours to 2000 hours. The scheduled coverage is requested by the method's logic where hospital staff is not generally available to do so during those hours.

The patient's interaction with the disclosed system via call, text, email, served web page or video 750 is monitored for ongoing patterns and response as well as post discharge medical outcome and patient satisfaction analysis. One or more topics or clinical processes 751 implemented with another computerized interactions are reported via text 752, call 753, or video interaction 754 with a care stakeholder or hospital command center. Any number of clinical processes and reporting of outputs can be configured into the hospital integrated IT system via use of mobile devices and network applications.

The patient may request a service response 755 to be in-person. A plurality of requests 756 may be sent as used for typically provided services such as a meal request 757 at a specific time or another service anytime between a given time span such as, for example, a chaplain call 759 within time period 758. The contact 760 may also be scheduled as part of the patient's care plan constructed by a healthcare provider or care stakeholders within parameters set by the healthcare provider. The patient may request a contact 760 by telephone call 761 via mobile device or video link 762, or via hospital landline phone 763 where calls are screened. Rather than patient requested contact, the provider request may also be part of a medical care plan derived by the care provider or care stakeholders within parameters set by the patient's healthcare provider.

Similar to running the status check for clinical logistics 735, the invention checks for patient services and communication coverage 765 and requests being met within an acceptable time duration. An acceptable time period may be characterized as a histogram 769 that corresponds to observed schedule variances 770. Upon discharge, a survey reveals results that indicate satisfaction scores 771 and cut-off points as to unsatisfactory and satisfactory care, among other categories as pre-determined by hospital operation. For example, a video chat with a patient is requested and scheduled anytime between 1400 hours and 1500 hours (772). From past observations, financial and other operations can be disruptive and cause time delay. For example, contacts made so many minutes 771 before 1400 hours or so many minutes after 1500 hours interfere with the hour scheduled, or run past 1500 hours to be disruptive to other activities and miss expectations. Here, patient expectations are being met correspond with the patient being satisfied with delivered care.

An objective of the disclosed invention is to coordinate care and monitor its delivery with an ability to interview the patient during the patient stay, or have the patient review the recorded "patient stay". If the plan is not being met, the patient's satisfaction declines, or the care stakeholder's satisfaction drops. A logical check is made over a duration of time, for example an hour, that patient visits and requests have been met. When requests are satisfied "√" 766, the duration of time is recorded as having met the plan. This recordation may be ongoing or determined in batch mode. Should a condition not be met, the period is so designated "x" 767. If an indeterminate satisfaction 768 exists, it is recorded as '-' 768.

For post survey causal analysis or for reviewing a patient's care plan with the patient, their stakeholders, or a regulating or review body, it is advantageous to consolidate the clinical and communication events that have occurred and create an integrated, composite view of the stay, ordered by time. Referring to FIG. 8, the stay replay is disclosed.

A consolidated, time ordered view of a patient's stay 800 is provided in one embodiment. Aspects of care, if conducted within time bounds, result in higher patient satisfaction scores, and the scores monitored with events recorded. These events may include, but are not limited to, rounding 810, nurse contact 815, clinical activity 820, patient call and care stakeholder response 825, visitor contact 830, patient feedback 835, requested in-situ activity and communications 840, stakeholder feedback 850, status checks of clinical logistics and patient coverage requests 855, structured and unstructured feedback points 860 (e.g. reasons for requests, contacts, events, response, etc.), and a composite summary 865.

Clinical rounding 810 for a plurality of patients are tracked by day 805, 808 and time durations 806, 807 by meaningful and definable clusters such as a clinician's shift. In a similar way for care stakeholders and activities, the events of the patient's stay are clustered by time bounds corresponding to meaningful sequences. For example, a certain patient visitor 830 was scheduled to support the patient's care process on days 805, 806 and times 806, 807. The stakeholder's performance is germane as to that scheduled period.

In one aspect, each care stakeholder is uniquely identified by tagged sensor as 816, 821, 831. Requested events 841 and feedback 851 are uniquely identified as well.

Patient feedback is provided by interactive devices owned by the hospital, the patient, or care stakeholders. Feedback is delivered with text or login to an installed application on a mobile or fixed device. Feedback may be a numerical score or graphic such as a "happy face" 836 or a "sad face" 837. Stakeholder feedback 850 is likewise attainable in metric or graphical form 852 from a plurality of inputs originating from mobile devices such as texts and calls 853 or via a photo 854 sent from a mobile device to a server or local code installed in a downloaded application. Aspects of the system 800 implement facial recognition or gesture recognition algorithms which classify feedback into numeric scores or summary graphical images. In another aspect, body or retinal scanning provides another mechanism for facial recognition and identification.

Stakeholder coverage and requests 855 are monitored and summarized 856, 857, 858 such that stay quality is assessed. A satisfactory assessment 856 (e.g. green code) has the attributes of having a person with a mobile device capable of monitoring with properly installed software and an ongoing pattern of inputs and outputs by that stakeholder with the device or the hospital's devices such that clinical logistics 730 and coverage 765 have been met. A lack of clinical logistics 730 and coverage 765, but establishment of monitoring presence and capability, for example, may be characterized as less robust or cautionary 857 (e.g. yellow code). Missed monitoring and missed logistical support 730 or patient requests 765 may be characterized as not robust or satisfactory 858 (e.g. red code). Causal factors 861 as reasons 860 for missed coverage of care performance are then listed.

A composite timeline of events and requests 865 is built from individual persons, events and status reports for both "stay replay" patient satisfaction anchoring at discharge as well as for outcomes and post survey diagnostics. An example composite activity log is a sequence beginning at 1200 hours on day 805 with a patient interaction 866 by care provider 725, a phone call 867 on the hospital line, a cell call 868, a care interaction 869 from a specific visitor 741 and a video call 870. The "as happened" versus plan 880 is compared for an assessment report as to whether the desired performance was met to satisfaction 881 or not satisfied 882 within the time period.

Having attained staffing, care schedules, monitored activities related to patient contact, and directed delivered care, a quantitative comparison of that care is analyzed according to the various stakeholders who span hospital staff and qualified visitors. Event data points are analyzed with respect to patient care quality feedback results, causal factors realized for continuous improvement in patient care, patient satisfaction assessed, and a provider's delivered care assessed along with various hospital operations.

Figure 9:
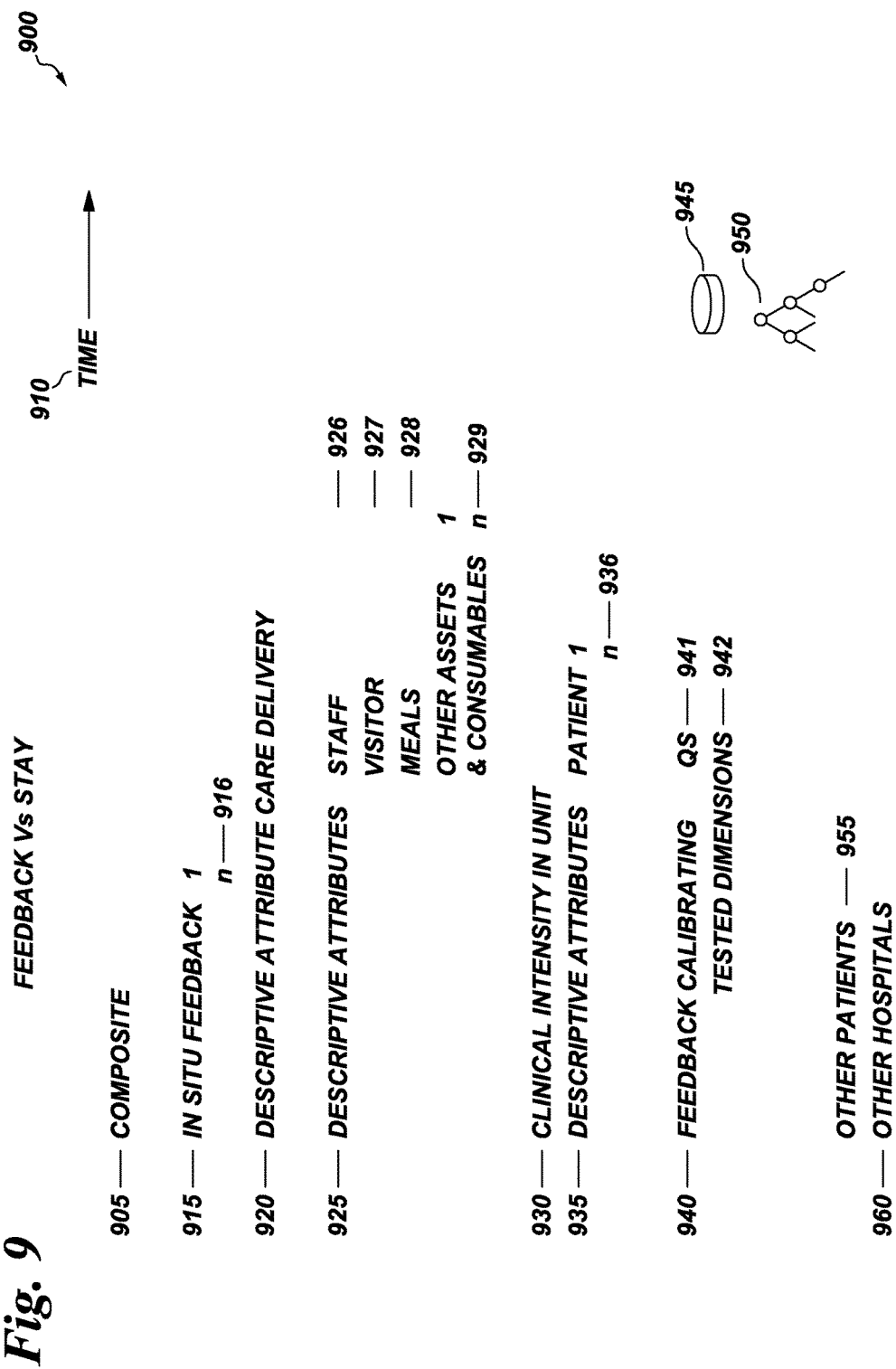
FIG. 9 provides a comparison between feedback and stay in embodiments of the invention.
Figure 10:
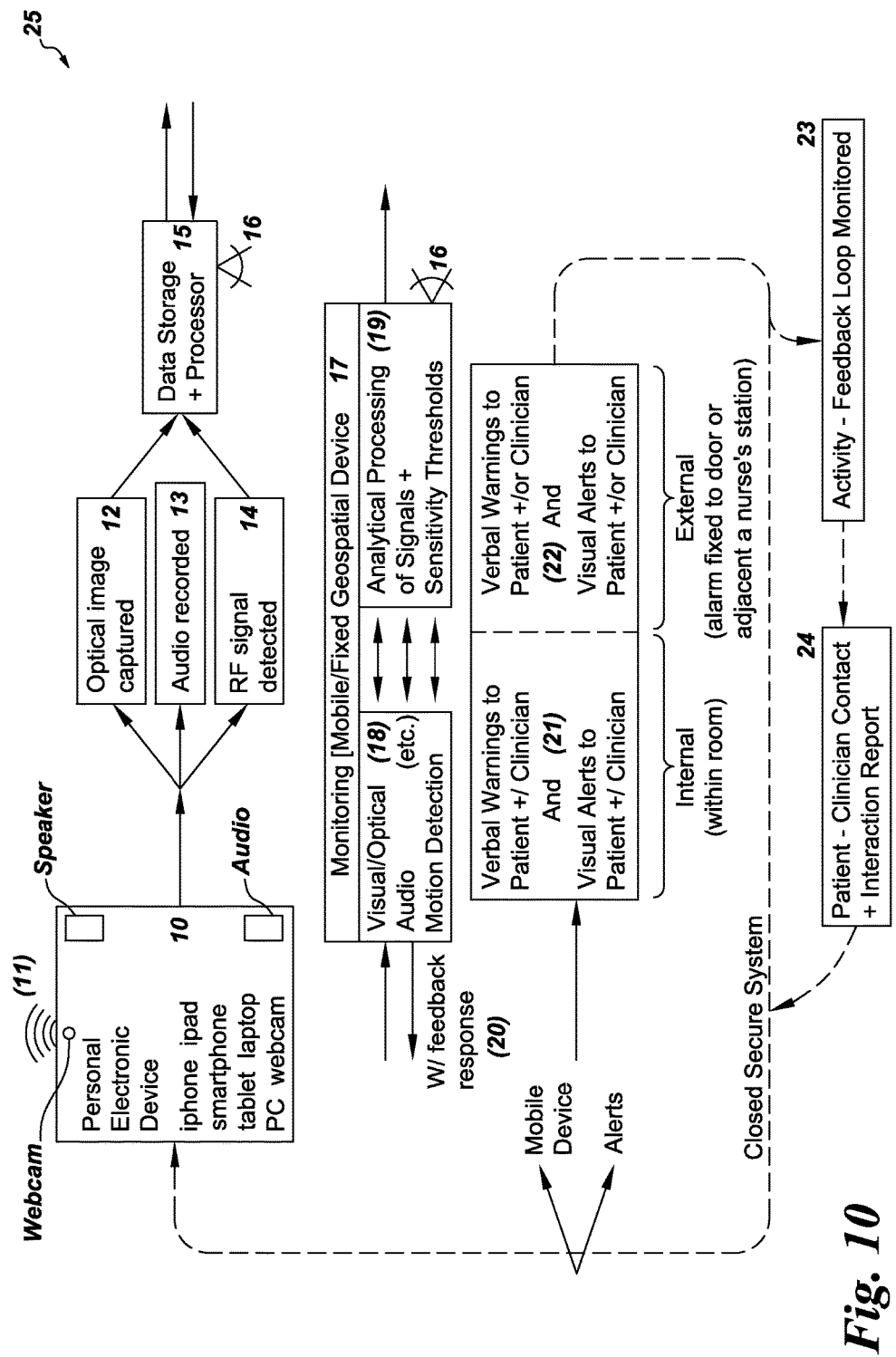
FIG. 10 depicts a schematic as to one embodiment of the invention.

Referring to FIG. 9, the method to improve hospital care quality as measured by patient and care stakeholder feedback by the use of commercially available connected mobile devices is disclosed in hospital operations system 900. The health care delivery process results are time ordered 910. Composite views 905 of coverage and requests, composite vs. plan and/or a benchmark 880, stakeholder coverage and requests made 855, durations of response times 769, duration acceptable settings 771, coverage probabilities 727 and their acceptable settings 728, requests met 765, logistics met 735, survey results 610, and any other aspect of recorded data disclosed herein and possible information captured with mobile or fixed devices orchestrated with the disclosed method and system, are aggregates in digital, searchable and computable form 945.

An example composite view 905 is a sequence of patient communication and contact 865. Patient and stakeholder feedback is enabled in real-time as time unfolds in situ 915 for stakeholders such as the patient 310, providers 330, and visitors 335, among others. Data is collected by specifically identifiable persons 916.

The descriptive attributes of the care being delivered 920 is attained as are those of people and assets and consumables used to deliver care 925 such as the employed or managed staff 926, visitors 927, meals 928, assets and other consumables 929. The clinical intensity 930 in a unit of the hospital is determined by census 931 on a unit, within a department or hospital wide, and by the clinical index such as patient case complexity and/or severity 932. Other assessed factors may include patient throughput or turnover, physician training, research or clinical studies, institute funding, affiliation with a University, etc. Attributes of the patient 935 and the evolving state of the patient over time 936 are attained.

With schedule, stakeholder, process, assets, and states of various care delivery inputs measured and recorded, the inputs are classified and subjected to statistical regression analytics transfer function 950. The output response is the result of in situ and post-stay feedback question results 940. To normalize feedback responses for various inputs, calibrating questions 941 are employed for one or more aspects 610 being surveyed. The response variable may be any other tested dimensions 942, intermediate step, result or output of the care delivery process which the disclosed system collects data for or enables. Embodiments of the system may utilize directed care plans and/or augmented reality. An example of the delivery process is using the clinical outcome state 943 of a patient as measured by accepted clinical measures, biometrics or second order observations such as re-admission rates. A single patient or a variety of patients may be included in the response objective 955. A hospital, a department, or cohort of the same may also be included in the comparative assessment 960.

A version of the interactive secure e-system 25 depicts a schematic as to movement of data and ongoing patient monitoring, alerts, and corrective action in a closed feedback system. The personal electronic device 10 is connected in the internet via a network connection signal 11, the device of which has an interconnected camera 12, audio recorder 13 and RF signal detector 14. In one aspect, the data capture components 12, 13, 14 are integral with the personal electronic device 10. Any data captured is sent to a storage component 15 which houses a data processor. Network connection 16 ensures the data is accessible to any connected network device and user interface having a network connection signal 11. Another mobile or fixed monitoring geospatial device 17 detects motion or audio and captures an image or recording 18, respectively, while the analytical processor 19 records signals and detects sensitivity thresholds as programmed during an established protocol. The analytical processor is interconnected with the network via the wireless network connection 16. A feedback response 20 stores the detected images, recordings, and signals for comparison and overlay of data so that the data is accessible via any secured personal electronic device. The data is shared in an update by way of a mobile device 10 and through an alert system that characterizes patient condition, warnings, or alerts at an internal location 21 within a patient's room and also at an external site 22 such as an alarm fixed to the exterior door or adjacent a nurse's station. The activity-feedback loop 23 is monitored and generates a patient-clinician contact and interaction report 24 accessible by any connected and secured personal electronic device in the system (as well as within the interconnected hospital operations and support infrastructure/IT systems). The closed secure system 25 continuously monitors protocol as specified in tasks that are triggered in the system, automated, or dependent on changes in image or audio as to a particular patient care setting. Thus, the system 25 provides nonstop, ongoing monitoring and patient care, immediate response to patient care needs and treatment plan, as well as improved response where protocol is not up to par or at a satisfactory level of patient satisfaction.

In various embodiments of the system, the personal electronic device may be a computer, iPhone®, iPad®, smartphone, tablet, personal computer (PC), laptop, interactive webcam, video, or recording device with data storage, direct image messaging system functionality (temporary or permanent), as well as any integrated social media or application (app) support from a mobile device so long as data is secured and respective of HIPAA rules and privacy to a patient and healthcare environment.

Embodiments of the invention also encompass various image capture devices such as laser range finders, optical scanners for body scanning or retinal imaging. Perhaps clinical devices are also integrated into the accessible data storage and processing such that ongoing vital sign measurements are recorded, tracked, and/or triggered by a particular feedback mechanism. For example, and not limitation, perhaps the image capture from a stationary room video camera senses motion of the patient. This triggers a vital sign such as respiratory rate, blood pressure, or pulse to be recorded. In another aspect, perhaps the webcam scans the room, collects various images and overlays the images upon one another for a collective scan report that details patient status, vital recordings, number of persons (visitors and/or clinicians in the room as indicated by their coded RF tags), temperature of the patient, temperature of the room, lighting, airflow, among others. The system operates to limit the number of clinicians required to be at the patient's bedside when a visitor is present or another staff member. With the rising costs of healthcare, increasing number of patients seeking healthcare, and reduced number of healthcare providers per patient population, systems such as the one disclosed provide high level patient care and interactive clinician support to the patient at a low cost.

The system can be modified to encompass any number of devices, as well as interact with systems integrated at various other hospitals that may be integrated with the same healthcare network or similar healthcare operations infrastructure.

Embodiments taught herein may be used in a variety of healthcare applications and to monitor a variety of care or management settings. Such information may be useful in many different types of settings throughout the hospital, within outpatient, ambulatory, inpatient settings, or within an at-home setting. Other systems may be integrated where personnel or student management tracks persons throughout a business setting or within an educational setting. For instance, public school systems that are overpopulated may find a cost need to interact with their teachers and students throughout the day, especially in emergency situations. The algorithms associated with the system can therefore be modified as to proposed use and protocol to support the environment and population within the particular setting.

Having thus described several exemplary embodiments of the invention, various alterations, modifications, and improvements will readily occur to those skilled in the art. For example, in some embodiments, such alterations, modifications, and improvements are intended to be part of this disclosure, and are intended to be within the scope of the invention. Accordingly, the foregoing description and drawings are by way of example only.

What is claimed is:

1. An integrated hospital information system for clinical decision support to monitor and report select data, the system comprising:
   a monitoring system comprising a plurality of data capture devices to generate a captured image of a patient's care and care setting, wherein the captured image includes a patient, a time duration, and a patient ID, the plurality of data capture devices comprising:
   a plurality of mobile devices each comprising:
      a camera configured to recognize tags in the care setting;
      at least one interface to receive information captured by the mobile device, wherein the information includes protocol, workflow, operational, and descriptive information, wherein the at least one interface records the captured image in real-time, and wherein the at least one interface comprises a network interface enabling internet access and access to a network; and
      at least one display generating a user interface by which a user selects data, wherein the at least one display displays an output report and an augmented reality image, wherein the output report comprises the data selected by the user, wherein the augmented reality image is received by the mobile device, and wherein the augmented reality image includes an updated captured virtual image;

at least one storage unit in the form of a server or a cloud-based storage connected to the network, wherein the storage unit stores recorded data from time ordered health care delivery process results and information captured by the plurality of data capture devices such that the recorded data and the information are aggregated in digital form capable of being digitally manipulated; and a processor comprising an analytics module that interacts with the at least one storage unit and the plurality of data capture devices, the analytics module configured to compute a quantitative comparison of clinical care based on communication with the patient, in terms of frequency, timing, and duration, and hospital staff responsiveness, the processor configured to:

receive the captured image from the plurality of data capture devices;

analyze the captured image relative to one or more protocols, wherein the one or more protocols include at least one of regulatory protocols, operating protocols, health provider orders, and a treatment of a patient or care plan;

determine, based upon the analysis, whether the captured image of the patient adheres to the one or more protocols;

store the captured image within the storage unit using the patient ID;

generate the updated captured virtual image by graphically overlaying, on the captured image, results based upon the analysis and determination; and publish, on the network, the updated captured virtual image such that the at least one display of the plurality of mobile devices displays the updated captured virtual image as the augmented reality image, wherein the augmented reality image provides ongoing patient monitoring and reporting of updates.

2. The system of claim 1, wherein the captured image is saved in the integrated hospital information system as a prior image and overlaid by the updated captured virtual image that provides overlaid action directives on the captured image and publishes on the network as a refreshed image that encompasses one or more action items or initiates real-time indicators to provide ongoing patient monitoring and reporting updates to a plurality of stakeholders.

3. The system of claim 1, wherein the analytics module produces outputs that result in augmented or annotated information delivered to at least one data capture device of the plurality of data capture devices.

4. The system of claim 3, wherein the captured image is a real-world observation by a user of the at least one data capture device of the plurality of data capture devices and produces a real-time image that overlays a graphic of a hospital room environment with a defined protocol.

5. The system of claim 4, wherein the graphic of the hospital room environment identifies one or more deviations from the defined protocol, and wherein the processor provides an alert at each of a plurality of user interfaces as integrated with each of the plurality of data capture devices including at least one of a site of the deviation, at a health care provider alert station, and on one or more mobile devices.

6. The system of claim 1, wherein the updated captured virtual image is updated continuously as evidence as to whether a defined protocol has been followed or not.

7. The system of claim 1, wherein the analytics module extracts a patient's identification and HIPAA information associated with a patient's identification tag or electronic medical record.

8. The system of claim 3, wherein the at least one data capture device of the plurality of data capture devices is a mobile device of a clinician to provide protocol support, treatment plans, and feedback.

9. The system of claim 3, wherein the at least one data capture device of the plurality of data capture devices is a mobile device of a patient to provide inputs into the system as to perceived well-being and status.

10. The system of claim 1, wherein the data capture device is a mobile device and receives information from said network along with said alert, such that the information is shared within a hospital unit or across multiple hospital units.

11. The system of claim 1, further comprising a patient's electronic medical records associated with a personalized treatment plan and published within the network whenever inputs or modifications are made.

12. The system of claim 11, further comprising a decision support system incorporated with the analytics module to report prior decisions made as to the personalized treatment plan, a prior treatment of the patient or care plan, and further recommending options as to future treatment.

13. The system of claim 1, wherein a plurality of inputs and a plurality of outputs are analyzed and recorded in the at least one storage unit for later recall and reporting.

14. The system of claim 1, further comprising a patient feedback system that implements a survey as to patient satisfaction and overall hospital operations.

15. The system of claim 1, wherein the integrated hospital information system for clinical decision support is based in a care setting comprising any one of: a hospital, a medical institute, a dental clinic, an outpatient clinic, a physician's office, a pharmaceutical setting, home environment, or other patient care setting.

16. A method for clinical decision support to monitor and report select data, said method implemented using an integrated hospital information system, said method comprising:

recording, by the integrated hospital information system, a captured image;

analyzing, by the integrated hospital information system, the captured image relative to one or more protocols, wherein the one or more protocols include at least one of regulatory protocols, operating protocols, health provider orders, and a treatment of a patient or care plan;

determining, by the integrated hospital information system, based upon the analysis, whether the captured image of the patient adheres to the one or more protocols;

storing, by the integrated hospital information system, the captured image within a storage unit using a patient ID;

generating, by the integrated hospital information system, an updated captured virtual image by graphically overlaying, on the captured image, results based upon the analysis and determination;

continually updating, by the integrated hospital information system, the captured image on a network while utilizing the updated captured virtual image; and publishing, on a network, by the integrated hospital information system, the updated captured virtual image such that a plurality of mobile devices displays the updated captured virtual image as an augmented reality image that includes the updated captured virtual image, wherein the augmented reality image provides ongoing patient monitoring and reporting of updates.

17. The method of claim 16, further comprising a step of reporting updates that are further utilized as an ongoing score of processes being met satisfactorily or unsatisfactorily to provide a validation process during post-process analytics.

18. The method of claim 16, further comprising scheduling coverage via the plurality of mobile devices networked to the integrated hospital information system to provide monitoring of directed care using one or more of a function of hospital staffing, type of services needed, and stakeholder availability.

19. The method of claim 18, wherein in said step of scheduling coverage, shift timing is adjusted throughout a 24 hour timeframe to accommodate patient care and staffing objectives.

20. The method of claim 19, wherein in said step of scheduling coverage, the staffing objectives accommodate physician, nurse, and staff availability, including staff shortages, surpluses, overtime, and use of temporary or agency staff.

21. The method of claim 16, wherein in said ongoing patient monitoring and reporting, the updates synchronize and publish to the plurality of mobile devices, a plurality of communication centers, and a plurality of health care providers in the form of text, picture, video, call, or web-enabled interface on a continuous basis or as determined per protocol and communication support.

22. The method of claim 16, wherein the integrated hospital information system utilizes a step of providing real-time patient care quality reports and a step of assessing a hospital's operational quality to produce patient satisfaction reports and hospital assessment, respectively.

23. The method of claim 16, further comprising a step of using mixed integer linear programming to provide optimization in the integrated hospital information system.

24. The method of claim 23, wherein the mixed integer linear programming utilizes a task component such that staffing is monitored per patient caseload and a shift prescribed for a specified hour and within a particular hospital.

25. The method of claim 24, wherein the shift prescribed triggers an inquiry in the integrated hospital information system for availability of staff, and creates new shifts or augments an existing shift by changing duration, start time, end time, or allocation of staff within or across units.

26. The method of claim 25, wherein the staff respond using a user interface to post and schedule real-time availability.

27. The method of claim 16, wherein the integrated hospital information system utilizes a decision support framework in combination with protocols or patient care needs to make dynamic decisions concerning assignment of staff to patients.

28. The method of claim 16, further comprising a target response time that is a control variable in a numerical simulation of a hospital care delivery process.

29. The method of claim 28, further comprising a cost to meet the target response time compared to a cost as to a variable response time, the compared cost correlated to a patient satisfaction score.

30. The method of claim 16, wherein the one or more protocols establish a threshold protocol that is dynamically adjusted based on learned information about a patient such that a duration for a plurality of patients is a function of personality, descriptive attributes, staff, visitors, and attributes known or determined to affect patient feedback.

31. The method of claim 30, wherein the duration engages stakeholders including physicians, nurses, staff, skilled hospitality, administration and visitors.

32. The method of claim 18, wherein a data capture device is used as a fixed monitoring modality to validate inputs from the plurality of mobile devices.

33. A method for clinical decision support to monitor and report select data, said method implemented using an integrated hospital information system, said method comprising:
  recording, by the integrated hospital information system, a captured image;
  analyzing, by the integrated hospital information system, the captured image relative to one or more protocols, wherein the one or more protocols include at least one of regulatory protocols, operating protocols, health provider orders, and a treatment of a patient or care plan;
  determining, by the integrated hospital information system, based upon the analysis, whether the captured image of the patient adheres to the one or more protocols;
  storing, by the integrated hospital information system, the captured image within a storage unit using a patient ID;
  generating, by the integrated hospital information system, an updated captured virtual image by graphically overlaying, on the captured image, results based upon the analysis and determination;
  continually updating, by the integrated hospital information system, the captured image on a network while utilizing the updated captured virtual image;
  publishing, on a network, by the integrated hospital information system, the updated captured virtual image such that a plurality of mobile devices displays the updated captured virtual image as an augmented reality image that includes the updated captured virtual image, wherein the augmented reality image provides ongoing patient monitoring and reporting of updates;
  designating, by the integrated hospital information system, at least one visit; and
  alerting, by the integrated hospital information system, a stakeholder of a missed visit.

34. A method for clinical decision support to monitor and report select data, said method implemented using an integrated hospital information system, said method comprising:
  recording, by the integrated hospital information system, a captured image;
  analyzing, by the integrated hospital information system, the captured image relative to one or more protocols, wherein the one or more protocols include at least one of regulatory protocols, operating protocols, health provider orders, and a treatment of a patient or care plan;
  determining, by the integrated hospital information system, based upon the analysis, whether the captured image of the patient adheres to the one or more protocols;
  storing, by the integrated hospital information system, the captured image within a storage unit using a patient ID;
  generating, by the integrated hospital information system, an updated captured virtual image by graphically overlaying, on the captured image, results based upon the analysis and determination;

continually updating, by the integrated hospital information system, the captured image on a network while utilizing the updated captured virtual image;

publishing, on a network, by the integrated hospital information system, the updated captured virtual image such that a plurality of mobile devices displays the updated captured virtual image as an augmented reality image that includes the updated captured virtual image, wherein the augmented reality image provides ongoing patient monitoring and reporting of updates; and monitoring, by the integrated hospital information system, a patient's care and care setting in real-time, wherein the integrated hospital information system stores, analyzes, and reports data with permissions and encryption with an edge device or by way of remote computing.

35. A method for clinical decision support to monitor and report select data, said method implemented using an integrated hospital information system, said method comprising:

recording, by the integrated hospital information system, a captured image;

analyzing, by the integrated hospital information system, the captured image relative to one or more protocols, wherein the one or more protocols include at least one of regulatory protocols, operating protocols, health provider orders, and a treatment of a patient or care plan;

determining, by the integrated hospital information system, based upon the analysis, whether the captured image of the patient adheres to the one or more protocols;

storing, by the integrated hospital information system, the captured image within a storage unit using a patient ID;

generating, by the integrated hospital information system, an updated captured virtual image by graphically overlaying, on the captured image, results based upon the analysis and determination;

continually updating, by the integrated hospital information system, the captured image on a network while utilizing the updated captured virtual image;

publishing, on a network, by the integrated hospital information system, the updated captured virtual image such that a plurality of mobile devices displays the updated captured virtual image as an augmented reality image that includes the updated captured virtual image, wherein the augmented reality image provides ongoing patient monitoring and reporting of updates; and managing a workflow that includes a plurality of tasks, wherein the plurality of tasks have interdependencies, and wherein a variation in the workflow alerts a care stakeholder to manage patient expectations.

\* \* \* \* \*